(12) United States Patent
Sohrabpour et al.

(10) Patent No.: US 10,945,622 B2
(45) Date of Patent: Mar. 16, 2021

(54) SYSTEM AND METHOD FOR ASSESSING ELECTRICAL ACTIVITY USING AN ITERATIVE SPARSE TECHNIQUE

(71) Applicant: REGENTS OF THE UNIVERSITY OF MINNESOTA, Minneapolis, MN (US)

(72) Inventors: Abbas Sohrabpour, Minneapolis, MN (US); Bin He, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 576 days.

(21) Appl. No.: 15/684,394

(22) Filed: Aug. 23, 2017

(65) Prior Publication Data

US 2018/0055394 A1   Mar. 1, 2018

Related U.S. Application Data

(60) Provisional application No. 62/378,609, filed on Aug. 23, 2016.

(51) Int. Cl.
*A61B 5/04* (2006.01)
*A61B 5/0476* (2006.01)
(Continued)

(52) U.S. Cl.
CPC ........ *A61B 5/04012* (2013.01); *A61B 5/0036* (2018.08); *A61B 5/0452* (2013.01);
(Continued)

(58) Field of Classification Search
None
See application file for complete search history.

(56) References Cited

U.S. PATENT DOCUMENTS

2009/0018432 A1* 1/2009 He .................. A61B 5/0093
                                                    600/409
2017/0332933 A1* 11/2017 Krishnaswamy .... A61B 5/0436

OTHER PUBLICATIONS

Gramfort et al., "Identifying Predictive Regions from fMRI with TV-L1 Prior", 2013 International Workshop on Pattern Recognition in Neuroimaging, IEEE, Jun. 22-24, 2013, Philadelphia, PA, pp. 17-20. (Year: 2013).*

(Continued)

*Primary Examiner* — Katherine L Fernandez
(74) *Attorney, Agent, or Firm* — Quarles & Brady LLP

(57) ABSTRACT

Three-dimensional electrical source imaging of electrical activity in a biological system (e.g., brain or heart) may involve sensor array recording, at multiple locations, of signals (e.g. electrical or magnetic signals) of electrical activity. An initial estimate of an underlying source is obtained. Edge sparsity is imposed on the estimated electrical activity to eliminate background activity and create clear edges between an active source and background activity. The initial estimate is iteratively reweighted and a series of subsequent optimization problems launched to converge to a more accurate estimation of the underlying source. Images depicting a spatial distribution of a source are generated based on the iteratively reweighted edge sparsity, and the time-course of activity for estimated sources generated. Iterative reweighting penalizes locations with smaller source amplitude based on solutions obtained in previous iterations, and continues until a desirable solution is obtained with clear edges. The objective approach does not require subjective thresholding.

28 Claims, 28 Drawing Sheets

(51) Int. Cl.
*A61B 5/0452* (2006.01)
*A61B 5/00* (2006.01)

(52) U.S. Cl.
CPC .......... *A61B 5/0476* (2013.01); *A61B 5/4836* (2013.01); *A61B 5/742* (2013.01); *A61B 5/04008* (2013.01); *A61B 5/4094* (2013.01); *A61B 2562/04* (2013.01)

(56) References Cited

OTHER PUBLICATIONS

Strohmeier et al., "Improved MEG/EEG source localization with reweighted mixed-norms", 2014 International Workshop on Pattern Recognition in Neuroimaging, IEEE, Jun. 4-6, 2014, Tubingen, Germany, pp. 1-4. (Year: 2014).*
Baillet S, Mosher J, Leahy R. Electromagnetic Brain Mapping. IEEE Trans. Signal Process 2001; 18:14-30.
Beck A, Teboulle M. A fast iterative shrinkage-thresholding algorithm for linear inverse problems. SIAM J. Imaging Sci. 2009; 2 (1): 183-202.
Bolstad A, Van Veen B, Nowak R. Space-Time event sparse penalizaion for magneto-/electroencephalography. NeuroImage. 2009; 46:1066-1081.
Candès E, Wakin M, Boyd S. Enhancing Sparsity by Reweighting L1 Minimization. J Fourier Anal. Appl. 2008; 14:877-905.
Ding L, He B. Sparse Source Imaging in Electroencephalography with Accurate Field Modeling. Human Brain Mapping 2008; 29:1053-67.
Ding L. Reconstructing cortical current density by exploring sparseness in the transform domain. Phys. Med. Biol. 2009; 54:2683-2697.
Gorodnitsky, I.F., George, J.S., Rao, B.D., 1995. Neuromagnetic source imaging with FOCUSS: a recursive weighted minimum norm algorithm. Electroencephalogr. Clin. Neurophysiol. 95 (21), 231-251.
Gramfort A, Strohmeier D, Haueisen J, Hmlinen M, Kowalski M. Time—frequency mixed-norm estimates: sparse M/EEG imaging with non-stationary source activations. NeuroImage. 2013a; 70: 410-422.
Hamalainen M, Ilmoniemi, R. Interpreting magnetic fields of the brain: Minimum norm estimates. Medical and Biological Engineering and Computing 1994; 32:35-42.
Hansen, P.C., 1990. Truncated singular value decomposition solutions to discrete ill-posed problems with ill-determined numerical rank. SIAM J Sci Stat Comput. 11, 503-518.
Haufe S, Nikulin V, Ziehe A, Muller K, Nolte G. Combining sparsity and rotational invariance in EEG/MEG source reconstruction. NeuroImage 2008; 42:726-38.
Huang, M.X., Dale, A.M., Song, T., Halgren, E., Harrington, D.L., Podgomy, I., Canive, J.M., Lewise, S., Lee, R.R., 2006. Vector-based spatial-temporal minimum L1-norm solution for MEG. NeuroImage 31, 1025-1037.
Matsuura, K., Okabe, Y., 1995. Selective minimum-norm solution of the biomagnetic inverse problem. IEEE Trans. Biomed. Eng. 42, 608-615.
Ou W, Hämäläinen M, Golland P. A distributed spatio-temporal EEG/MEG inverse solver. Neuroimage. 2008; 44: 932-946.
Pascual-Marqui RD, Michel C, Lehmann D. Low resolution electromagnetic tomography: a new method for localizing electrical activity in the brain. Int. J. Psychophysiol. 1994; 18:49-65.
Tibshirani R. Regression Shrinkage and Selection via Lasso. J. R. Statist. Soc. 1996; 58:267-88.
Wipf D, Nagarajan S. Iterative reweighted L1 and L2 methods for finding sparse solutions. IEEE J. Sel. Top. Sign. Proces. 2010; 4 (2): 317-329.
Zhu, M., Zhang, W., Dickens, D.L., and Ding, L. Reconstructing spatially extended brain sources via enforcing multiple transform sparseness. NeuroImage 2014: 86:280-93.

* cited by examiner

SYSTEM AND METHOD FOR ASSESSING ELECTRICAL ACTIVITY USING AN ITERATIVE SPARSE TECHNIQUE

CROSS-REFERENCE TO RELATED APPLICATIONS

This application is based on, claims priority to, and incorporates herein by reference in its entirety U.S. Provisional Application Ser. No. 62/378,609, filed Aug. 23, 2016, and entitled, "System and Method for Assessing Neuronal Activity Using an Iterative Sparse Technique." The references cited in the above provisional patent application are also hereby incorporated by reference.

STATEMENT REGARDING FEDERALLY SPONSORED RESEARCH

121 This invention was made with government support under EB006433, NS096761, and EB021027 awarded by the National Institutes of Health. The government has certain rights in the invention.

FIELD OF THE INVENTION

This document relates to systems and methods for iteratively reweighted edge sparsity minimization strategies for obtaining information regarding the location and extent of the underlying sources of electrical activity in biological systems such as the brain and heart.

BACKGROUND

Electroencephalography (EEG)/magnetoencephalography (MEG) source imaging is used to estimate the underlying brain activity from scalp recorded EEG/MEG signals. The locations within the brain involved in a cognitive or pathological process can be estimated using associated electromagnetic signals such as scalp EEG or MEG. The process of estimating underlying sources from scalp measurements is a type of inverse problem referred to as electrophysiological source imaging (ESI).

There are two main strategies to solve the EEG/MEG inverse problem (source imaging), namely the equivalent dipole models, and the distributed source models. The dipole models assume that the electrical activity of the brain can be represented by a small number of equivalent current dipoles (ECD) thus resulting in an over-determined inverse problem. This, however leads to a nonlinear optimization problem, which ultimately estimates the location, orientation and amplitude of a limited number of equivalent dipoles, to fit the measured data. The number of dipoles has to be determined a priori. On the other hand, the distributed source models use a large number of dipoles or monopoles distributed within the brain volume or the cortex. In such models, the problem becomes linear, since the dipoles (monopoles) are fixed in predefined grid locations, but the model is highly underdetermined as the number of unknowns is much more than the number of measurements. Given that functional areas within the brain are extended and not point-like, the distributed models are more realistic. Additionally, determining the number of dipoles to be used in an ECD model is not a straightforward process.

Solving under-determined inverse problems calls for regularization terms (in the optimization problem) or prior information regarding the underlying sources. Weighted minimum norm solutions were one of the first and most popular algorithms. In these models, the regularization term is the weighted norm of the solution. Such regularization terms will make the process of inversion (going from measurements to underlying sources) possible and will also impose additional qualities to the estimation such as smoothness or compactness. Depending on what kind of weighting is used within the regularization term, different solutions can be obtained. If a uniform weighting or identity matrix is used, the estimate is known as the minimum norm (MN) solution. The MN solution is the solution with least energy (L2 norm) within the possible solutions that fit the measurements. It is due to this preference for sources with a small norm that MN solutions are well-known to be biased towards superficial sources. One modification to this setback is to use the norm of the columns of the lead field matrix to weight the regularization term in such a manner to penalize superficial sources more than the deep sources, as the deep sources do not present well in the scalp EEG/MEG. In this manner the tendency towards superficial sources is alleviated. This is usually referred to as the weighted minimum norm (WMN) solution. Another popular choice is the low resolution brain electromagnetic tomography (LORETA); if the source space is limited to the cortex, the inverse algorithm is called cortical LORETA (cLORETA). LORETA is basically a WMN solution where the weighting is a discrete Laplacian. The solution's second spatial derivative is minimized so the estimation is smooth. Many inverse methods apply the L2 norm, i.e. Euclidean norm, in the regularization term. This causes the estimated solution to be smooth, resulting in solutions that are overly smoothed and extended all over the solution space. Determining the active cortical region by distinguishing desired source activity from background activity (to determine source extent) proves difficult in these algorithms, as the solution is overly smooth and poses no clear edges between background and active brain regions (pertinent or desired activity, epileptic sources for instance as compared to background activity or noise). This is one major drawback of most conventional algorithms including the ones discussed so far, as a subjective threshold needs to be applied to separate pertinent source activity from noisy background activity.

In order to overcome the overly smooth solutions, the L2 norm can be supplanted by the L1 norm. This idea is inspired from sparse signal processing literature where the L1 norm has been proposed to model sparse signals better and more efficiently, specifically after the introduction of the least absolute shrinkage selection operator (LASSO). While optimization problems involving L1 norms do not have closed form solutions, they are easy to solve as they fall within the category of convex optimization problems (see Boyd & Vandenberghe, *Convex Optimization*, Cambridge University Press, 2004).

Selective minimum norm method, minimum current estimate and sparse source imaging are examples of such methods. These methods seek to minimize the norm of the solution. Another algorithm in this category, which uses a weighted minimum L1 norm approach to improve the stability and "spiky-looking" character of L1-norm approaches, is the vector-based spatio-temporal analysis using L1-minimum norm (VESTAL). These algorithms encourage extremely focused solutions. Such unrealistic solutions root from the fact that by penalizing the L1 norm of the solution a sparse solution is being encouraged. Under proper conditions regularizing the L1 norm of a solution will result in a sparse solution; a solution which has only a few number of non-zero elements. Sparsity is not a desired quality for underlying sources which produce EEG/MEG signals as EEG/MEG signals are the result of synchronous activity of neurons from a certain extended cortical region.

To overcome the aforementioned shortcomings while still benefiting from the advantages of sparse signal processing techniques, new regularization terms which encourage sparsity in other domains have been proposed. The idea is to find a domain in which the solution has a sparse representation. This basically means that while the solution might not be sparse itself (as is usually the case for underlying sources generating the EEG/MEG) it still might be sparsely represented in another domain such as the spatial gradient or wavelet coefficient domain. This amounts to the fact that the signal still has redundancies that can be exploited in other domains.

Prior solutions cannot yet determine the extent of the underlying source objectively, i.e. a subjective threshold (e.g. a certain percentage of activity relative to the maximum activity are kept) still needs to be applied to reject the background activity. In other approaches, functions which are believed to model the underlying source activity of the brain are defined a priori in a huge data set called the dictionary, and a solution which best fits measurements is sought within the dictionary. But in order to be unbiased and to avoid selecting parameters a priori (like subjective thresholding) the dictionary can be huge and the problem might become intractable. What is needed is an objective approach to solving the inverse problem that does not assume any prior dictionaries or basis functions and that does not require subjectively selecting a cutoff threshold to separate background electrical activity of the brain from active sources.

SUMMARY OF THE PRESENT DISCLOSURE

In various embodiments, a system for three-dimensional electrical source distribution imaging of electrical activity in a biological system comprises: a sensor array configured to record, at multiple locations, signals generated by the electrical activity in a biological system; a processor configured to: use the sensor array to record signals by the electrical activity in the biological system; generate an initial estimate of an underlying source distribution; impose edge sparsity on the estimated electrical activity to eliminate background activity and create clear edges between an active source and background activity; iteratively reweight a prior estimate and launch a series of subsequent optimization problems to converge to a more accurate estimation of the underlying source distribution; and generate one or more images depicting a spatiotemporal distribution of a source in the biological system using the iteratively reweighted edge sparsity.

In certain implementations, the processor is configured to generate the one or more images without application of a subjective threshold requirement for a magnitude of an electrical activity characteristic.

In certain implementations, the processor is configured, during iterative reweighting, to penalize locations which have smaller source amplitude based on solutions obtained in previous iterations, wherein iterative reweighting continues until a desirable solution is obtained with clear edges.

In certain implementations, the processor is configured to generate a series of images or a movie depicting spread, in time, of electrical activity through the biological system.

In certain implementations, the sensor array is configured to record electrical signals generated by electrical activity through the biological system.

In certain implementations, the sensor array is configured to record magnetic signals generated by electrical activity through the biological system.

In certain implementations, the sensor array is configured to record both electrical and magnetic signals generated by electrical activity through the biological system.

In certain implementations, imposing edge sparsity imposes edge sparsity on both a solution and a gradient of the solution.

In certain implementations, the biological system is a brain, and the sensor array is configured to record signals of electrical activity in the brain of a subject.

In certain implementations, the biological system is a heart, and the sensor array is configured to record signals of electrical activity in the heart of a subject.

In certain implementations, the generated image visually depicts location and extent of an electrical source at a given time.

In certain implementations, the generated images visually depict locations and extents of an electrical source over time.

In certain implementations, the processor is configured to obtain source extent by adding an edge-sparse term into a source optimization solution.

In certain implementations, the processor is further configured to display the generated image on a display device.

In various embodiments, a method for three-dimensional source distribution imaging of electrical activity in a biological system comprises: receiving signals recorded, using a sensor array, at multiple locations in a biological system; generating an initial estimate of an underlying source; imposing edge sparsity on the estimated electrical activity to eliminate background activity and create clear edges between an active source and background activity; iteratively reweighting a prior estimate and launch a series of subsequent optimization problems to converge to a more accurate estimation of the underlying source; and generating one or more images depicting a spatiotemporal distribution of a source in the biological system using the iteratively reweighted edge sparsity.

In certain implementations of the method, the one or more images are generated without application of a subjective threshold requirement for a magnitude of an electrical activity characteristic.

In certain implementations of the method, the processor is configured, during iterative reweighting, to penalize locations which have smaller source amplitude based on solutions obtained in previous iterations, wherein iterative reweighting continues until a desirable solution is obtained with clear edges.

In certain implementations of the method, the one or more images depict spread, in time, of electrical activity through the biological system.

In certain implementations of the method, the sensor array is configured to record electrical signals generated by electrical activity through the biological system.

In certain implementations of the method, the sensor array is configured to record magnetic signals generated by electrical activity through the biological system.

In certain implementations of the method, the sensor array is configured to record both electrical and magnetic signals generated by electrical activity through the biological system.

In certain implementations of the method, imposing edge sparsity imposes edge sparsity on both a solution and a gradient of the solution.

In certain implementations of the method, the biological system is a brain, and the sensor array records signals generated by electrical activity in the brain of a subject.

In certain implementations of the method, the biological system is a heart, and the sensor array records signals generated by electrical activity in the heart of a subject.

In certain implementations of the method, the generated image visually depicts location and extent of an electrical source at a given time.

In certain implementations of the method, the generated images visually depict locations and extents of an electrical source over time.

In certain implementations of the method, the processor is configured to obtain source extent by adding an edge-sparse term into a source optimization solution.

In various embodiments, a non-volatile storage medium has instructions for three-dimensional source distribution imaging of electrical activity in a biological system, the instructions, when executed by a processor, being configured to: receive recorded signals of electrical activity, using a sensor array, at multiple locations in a biological system; generate an initial estimate of an underlying source; impose edge sparsity on the estimated electrical activity to eliminate background activity and create clear edges between an active source and background activity; iteratively reweight a prior estimate and launch a series of subsequent optimization problems to converge to a more accurate estimation of the underlying source; and generate one or more images depicting a spatiotemporal distribution of a source in the biological system using the iteratively reweighted edge sparsity.

Disclosed are embodiments of an iteratively reweighted edge sparsity minimization (IRES) strategy that can be used, for example, to estimate the source location and extent from electrical or/and magnetic signals of a biological system. As demonstrated, using sparse signal processing techniques, it is possible to extract information, objectively, about the extent of the underlying source. IRES have been demonstrated in a series of computer simulations and tested in epilepsy patients undergoing intracranial EEG recordings and surgical resections. Additionally IRES has been implemented in an efficient spatio-temporal framework, making IRES suitable for studying dynamic brain sources over time. Simulations and clinical results indicate that IRES provides source solutions that are spatially extended without the need to threshold the solution to separate background activity from active sources under study. This gives IRES a unique standing within the existing body of inverse imaging techniques. IRES may be used for source extent estimation from noninvasive EEG/MEG, which can be applied to epilepsy source imaging, determining the location and extent of the underlying epileptic source. The techniques can also be applied to other brain imaging applications including normal brain functions or other brain disorders, or electrical activity originated from out of the brain such as the heart and muscles.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the invention.

BRIEF DESCRIPTION OF THE DRAWINGS

The drawings illustrate generally, by way of example, but not by way of limitation, various embodiments discussed in the present document.

Figure 1:
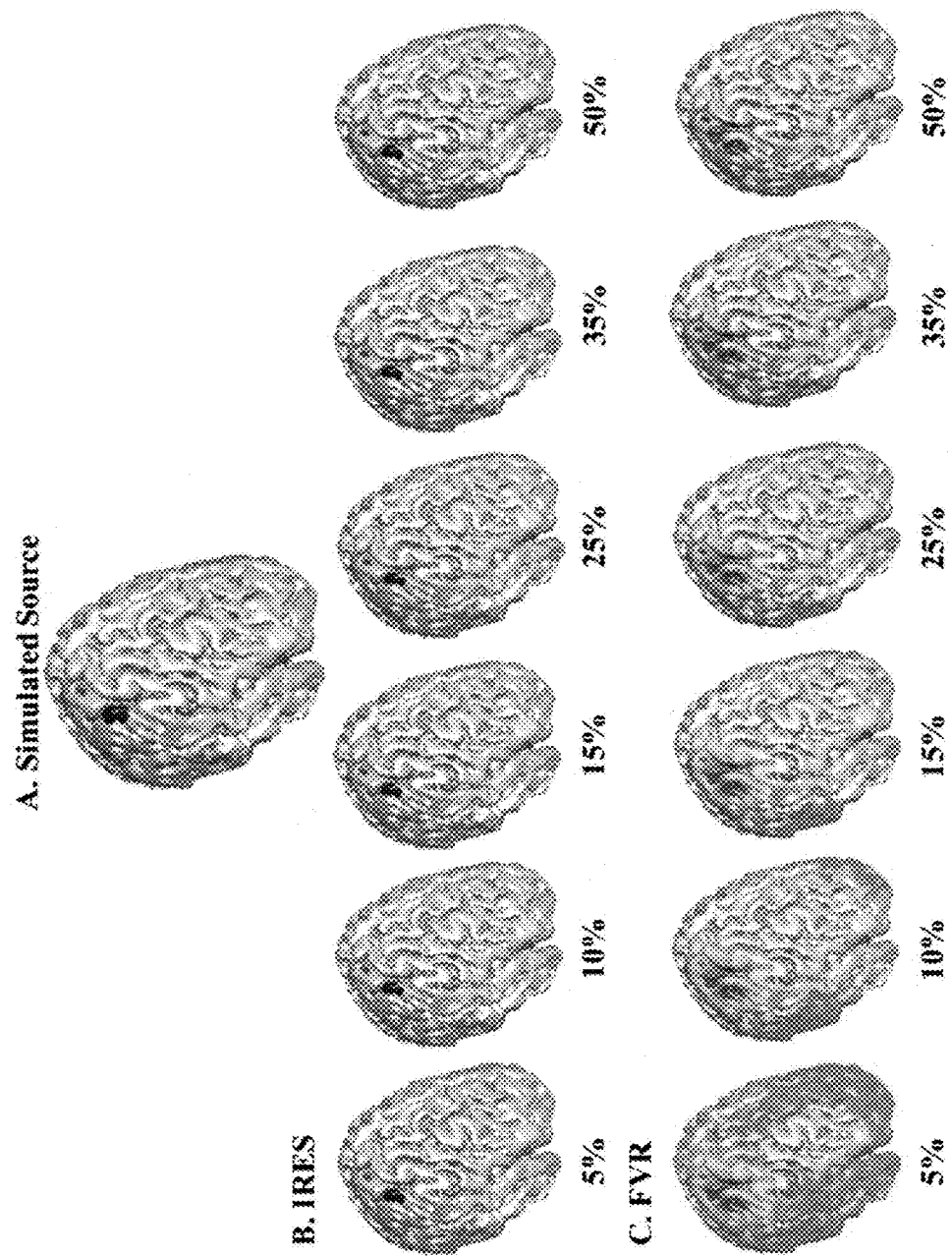
FIG. 1 illustrates the effect of thresholding on iteratively reweighted edge sparsity minimization (IRES) versus focal vector field reconstruction (FVR). Thresholds of different value (from 5% to 50%) are applied to the solutions derived from IRES and FVR. As can be seen, IRES does not use a set value of threshold to separate background from active sources and hence is unaffected by thresholding. The data-driven iterations within the total-variation (TV) framework automatically eliminate background activity and create clear edges between active sources and background activity.

It should be appreciated that the figures are intended to be generally illustrative, not limiting, of principles related to example embodiments and implementations of the disclosure.

DETAILED DESCRIPTION OF THE PRESENT DISCLOSURE

Estimating the extent of an underlying source is a challenge but also highly desirable in many applications. Determining the epileptogenic brain tissue is one important application. EEG/MEG source imaging is a non-invasive technique making its way into the presurgical workup of epilepsy patients undergoing surgery. EEG/MEG source imaging helps the physician in localizing the location of activity and if it can more reliably and objectively estimate the extent of the underlying epileptogenic tissue, the potential merits to improve patient care and quality of life are obvious since EEG and MEG are noninvasive modalities. Another important application is mapping brain functions, elucidating roles of different regions of the brain responsible for specific functional tasks using EEG/MEG. This approach is applicable to non-brain applications as well, such as electrical activity in, for example, the heart or other biological systems. It should be appreciated that the below discussion of brain applications provides examples that illustrate principles that are also applicable to non-brain applications.

In order to devise an algorithm that is able to objectively determine the extent of the underlying sources, multiple domain sparsity and iterative reweighting within the sparsity framework are introduced to achieve this goal. If the initial estimation of the underlying source is relaxed enough to provide an overestimation of the extent, it is possible to use this initial estimation and launch a series of subsequent optimization problems to gradually converge to a more accurate estimation of the underlying source. The sparsity is imposed on both the solution and the gradient of the solution. This is the basis of example embodiments of the disclosed approach, which is referred to as iteratively reweighted edge sparsity minimization (IRES) for convenience.

The notion of edge sparsity or imposing sparsity on the gradient of the solution is also sometimes referred to as the total-variation (TV) in image processing literature. Recently some fMRI studies have shown the usefulness of working within the TV framework to obtain focal hot-spots within fMRI maps without noisy spiky-looking results. The results presented in prior studies still need to set a threshold to reject background activity. The approach that may be used in IRES, by contrast, is initiating a sequence of reweighting iterations based on obtained solutions to suppress background activity and creating clear edges between sources and background. One example has been presented in FIG. 1 to show the effect of thresholding on IRES estimates.

A series of computer simulations were performed to assess the performance of the IRES algorithm in estimating source extent from the scalp EEG. The estimated results were compared with the simulated target sources and quantified using different metrics. To show the usefulness of IRES in determining the location and extent of the epileptogenic zone in case of focal epilepsy, the algorithm has been applied to source estimation from scalp EEG recordings and compared to clinical findings such as surgical resection and seizure onset zone (SOZ) determined from intracranial EEG by the physician.

Example Implementations—IRES

The brain electrical activity can be modeled by current dipole distributions. The relation between the current dipole distribution and the scalp EEG/MEG is constituted by Maxwell's equations. After discretizing the solution space and numerically solving Maxwell's equations, a linear relationship between the current dipole distribution and the scalp EEG/MEG can be derived:

$$\varphi = Kj + n_0 \quad (1)$$

where $\varphi$ is the vector of scalp EEG (or MEG) measurements, K is the lead field matrix which can be numerically calculated using the boundary element method (BEM) modeling, j is the vector of current dipoles to be estimated and $n_0$ models the noise. For EEG source imaging, $\varphi$ is an M×1 vector, where M refers to the number of sensors; K is an M×D matrix, where D refers to the number of current dipoles; j is a vector of D×1, and $n_0$ is an M×1 vector.

Following the multiple domain sparsity in the regularization terms, the optimization problem is formulated as a second order cone programming (SOCP) in equation (2). While problems involving L1 norm minimization do not have closed-form solutions and may seem complicated, such problems can readily be solved as they fall within the convex optimization category. There are multiple methods for solving convex optimization problems.

$$j^{est} = \underset{j}{\operatorname{argmin}} \|Vj\|_1 + \alpha\|j\|_1 \quad (2)$$

$$\text{subject to } (\varphi - Kj)^T \sum\nolimits^{-1} (\varphi - Kj) \leq \beta$$

Where V is the discrete gradient defined based on the source domain geometry (T×D, where T is the number of edges as defined by equation (4), below), $\beta$ is a parameter to determine noise level and $\Sigma$ is the covariance matrix of residuals, i.e. measurement noise covariance. Under the assumption of additive white Gaussian noise (AWGN), $\Sigma$ is simply a diagonal matrix with its diagonal entries corresponding to the variance of noise for each recording channel. In more general and realistic situations, $\Sigma$ is not diagonal and has to be estimated from the data (refer to simulation protocols for more details on how this can be implemented). Under the uncorrelated Gaussian noise assumption it is easy to see that the distribution of the residual term will follow the $\chi_n^2$ distribution, where $\chi_n^2$ is the chi-squared distribution with n degrees of freedom (n is the number of recording channels, i.e. number of EEG/MEG sensors). In case of correlated noise, the noise whitening process in (2) will eliminate the correlations and hence is an important step. This de-correlation process is achieved by multiplying the inverse of the covariance matrix ($\Sigma^{-1}$) by the residuals, as formulated in the constraint of the optimization problem in (2). In order to determine the value of $\beta$ the discrepancy principle is applied. This translates to finding a value for $\beta$ for which it can be guaranteed that the probability (p) of having the residual energy within the [0, $\beta$] interval is high (p). Setting p=0.99, $\beta$ was calculated using the inverse cumulative distribution function of the $\chi_n^2$ distribution.

The optimization problem disclosed in (2) is an SOCP-type problem that is solved at every iteration of IRES. In each iteration, based on the estimated solution, a weighting coefficient is assigned to each dipole location. Intuitively, locations which have dipoles with small amplitude will be penalized more than locations which have dipoles with larger amplitude. In this manner, the optimization problem will gradually slim down to a better estimate of the underlying source. The details of how to update the weights at each iteration and why to follow such a procedure is given below in Appendix A. Mathematically speaking, the following procedure can be repeated until the solution does not change significantly in two consecutive iterations as outlined in (3):

At iteration L:

$$j^L = \underset{j}{\operatorname{argmin}} \|W_d^{L-1}(Vj)\|_1 + \alpha\|W^{L-1}j\|_1 \quad (3)$$

$$\text{subject to } (\varphi - Kj^L)^T \sum\nolimits^{-1} (\varphi - Kj^L) \leq \beta$$

where $W^L$ and $W_d^L$ are updated based on the estimation $j^L$ (further discussed below).

Figure 2:
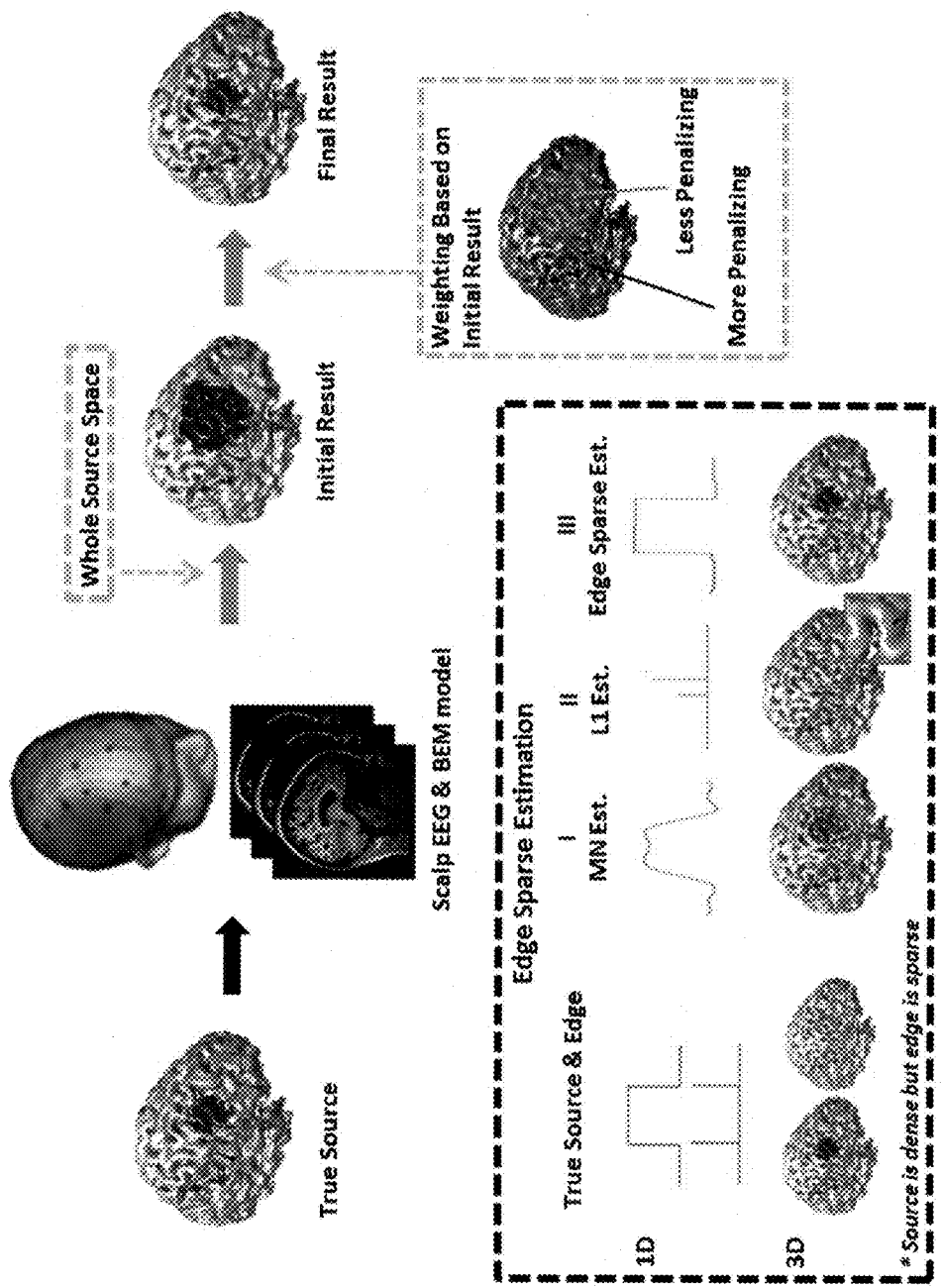
FIG. 2 provides a schematic diagram representing the IRES approach in accordance with one or more embodiments. Two strategies (edge sparse estimation and iterative reweighting) accurately estimate the source extent. The edge sparse estimation is based on the prior information that source is densely distributed but the source edge is sparse. The source extent can thus be obtained by adding the edge-sparse term into the source optimization solution. The iterative reweighting is based on a multi-step approach. Initially an estimate of the underlying source is obtained. Consequently the locations which have less activity (smaller source amplitude) are penalized based on the solutions obtained in previous iterations. This process may be continued until a desirable solution is obtained with clear edges.

The procedure is depicted in FIG. 2. The idea of data-driven weighting is schematically depicted. Although the number of iterations cannot be determined a priori, the solution converges pretty fast, usually within two to three iterations. One of the advantages of IRES is that it uses data-driven weights to converge to a spatially extended source. Following the idea proposed in the sparse signal processing literature, the heuristic that locations with smaller dipole amplitude should be penalized more than other locations, will be formalized. In the sparse signal processing literature it is well known that under some general conditions the L1-norm can produce sparse solutions; in other words "L0-norm" can be replaced with L1-norm. In reality, "L0-norm" is not really a norm, mathematically speaking. It assigns 0 to the elements of the input vector when those elements are 0 and 1 otherwise. When sparsity is considered, such a measure or pseudo-norm is intended (as this measure will impose the majority of the elements of the vector to be zero, when minimized). However this measure is a non-convex function and including it in an optimization problem makes it hard or impossible to solve, so it is replaced by the L1-norm which is a convex function and under general conditions the solutions of the two problems are close enough. When envisioning "L0-norm" and L1-norm, it is evident that while "L0-norm" takes a constant value as the norm of the input vector goes to infinity, L1-norm is unbounded and goes to infinity. In order to use a measure which better approximates the L0-norm and yet has some good qualities (for the optimization problem to be solvable), some have proposed that a logarithm function be used instead of the "L0-norm". Logarithmic functions are concave but also quasi-convex, thus the problem would be solvable. However, finding the global minimum (which is a promise in the convex optimization problems) is no more guaranteed. This means that the problem is replaced with a series of optimization problems, which could converge to a local minimum; thus the final outcome of the problem depends on the initial estimation. Our results in this paper indicate that initiating the problem formulated in (3) with identity matrices, provide good estimates in most of the cases, hopefully indicating that the algorithm might not be getting trapped in local minima. More detailed mathematical analysis is presented in Appendix A.

Figure 3:
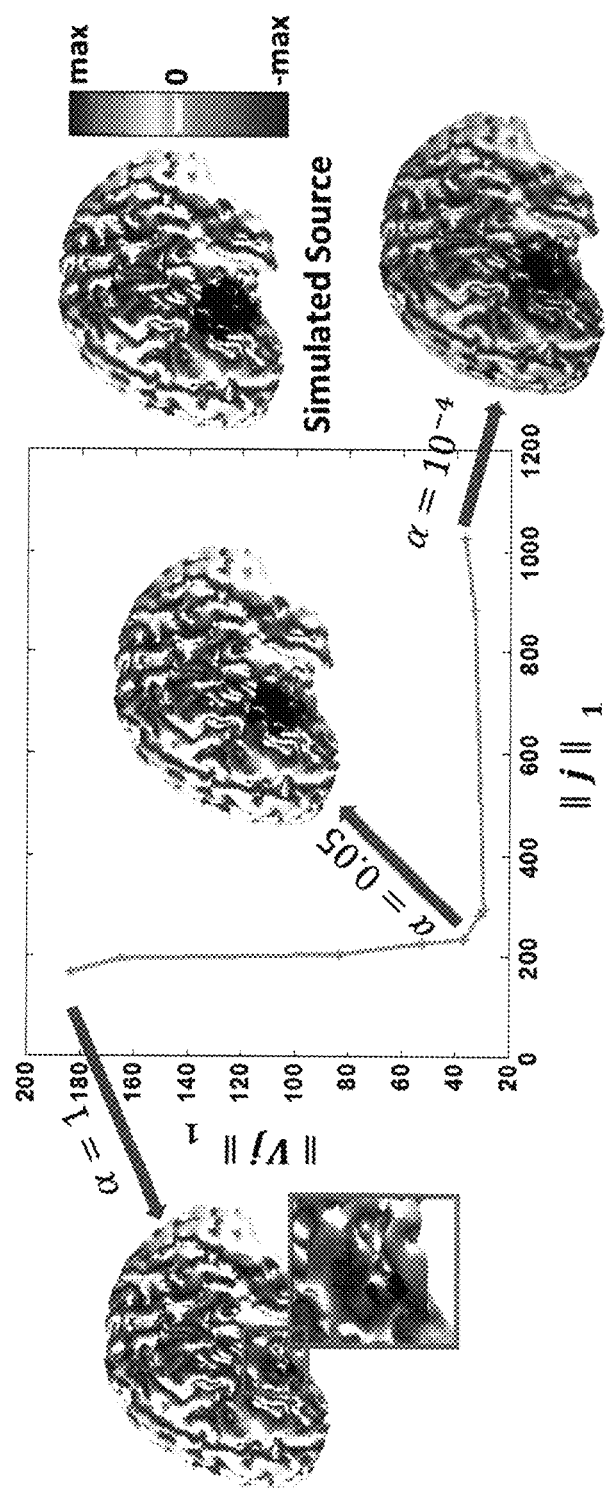
FIG. 3 illustrates selecting the hyper-parameter $\alpha$ using the L-curve technique. In order to select $\alpha$, which is a hyper-parameter balancing between the sparsity of the solution and gradient domain, the L-curve technique is adopted. As it can be seen a large value of $\alpha$ will encourage a sparse solution while a small value of $\alpha$ encourages a piecewise constant solution which is over-extended. The selected $\alpha$ is a compromise. Looking at the curve it seems that an $\alpha$ corresponding to the knee is optimum as perturbing $\alpha$ will make either of the terms in the goal function grow and thus would not be optimal. The L-curve in this figure is obtained when a source with an average radius of 20 mm was simulated. The SNR of the simulated scalp potential is 20 dB.

Selecting the hyper-parameter α is not a trivial task. Selecting hyperparameters can be a dilemma in any optimization problem and most optimization problems inevitably face such a selection. In example implementations, the L-curve approach may be used to objectively determine the suitable value for α. Referring to FIG. 3 it can be seen how selecting different values for α can affect the problem. In this example a 20 mm extent source is simulated and a range of different α values ranging from 1 to $10^{-4}$ are used to solve the inverse problem. As it can be seen, selecting a large value for α will result in an overly focused solution (underestimation of the spatial extent). This is due to the fact that by selecting a large value for α the optimization problem focuses more on the L1-norm of the solution rather than the domain sparsity (TV term) so the solution will be sparse. In the extreme case when α is much larger than 1 the optimization problem turns into a L1 estimation problem which is known to be extremely sparse, i.e. focused. Conversely selecting very small values for α may result in spread solutions (overestimation of the spatial extent). Selecting an α value near the bend (knee) of the curve is a compromise to get a solution which minimizes both terms involved in the regularization. The L-curve basically looks at different terms within the regularization and tries to find an α for which all the terms are small and also changing α minimally along each axis will not change the other terms drastically. In other words the bend of the L-curve gives the optimal α as changing α will result in at least one of the terms in the regularization term to grow which is counterproductive in terms of minimizing (2). In this example an α value of 0.05 to 0.005 achieves reasonable results.

Figure 4:
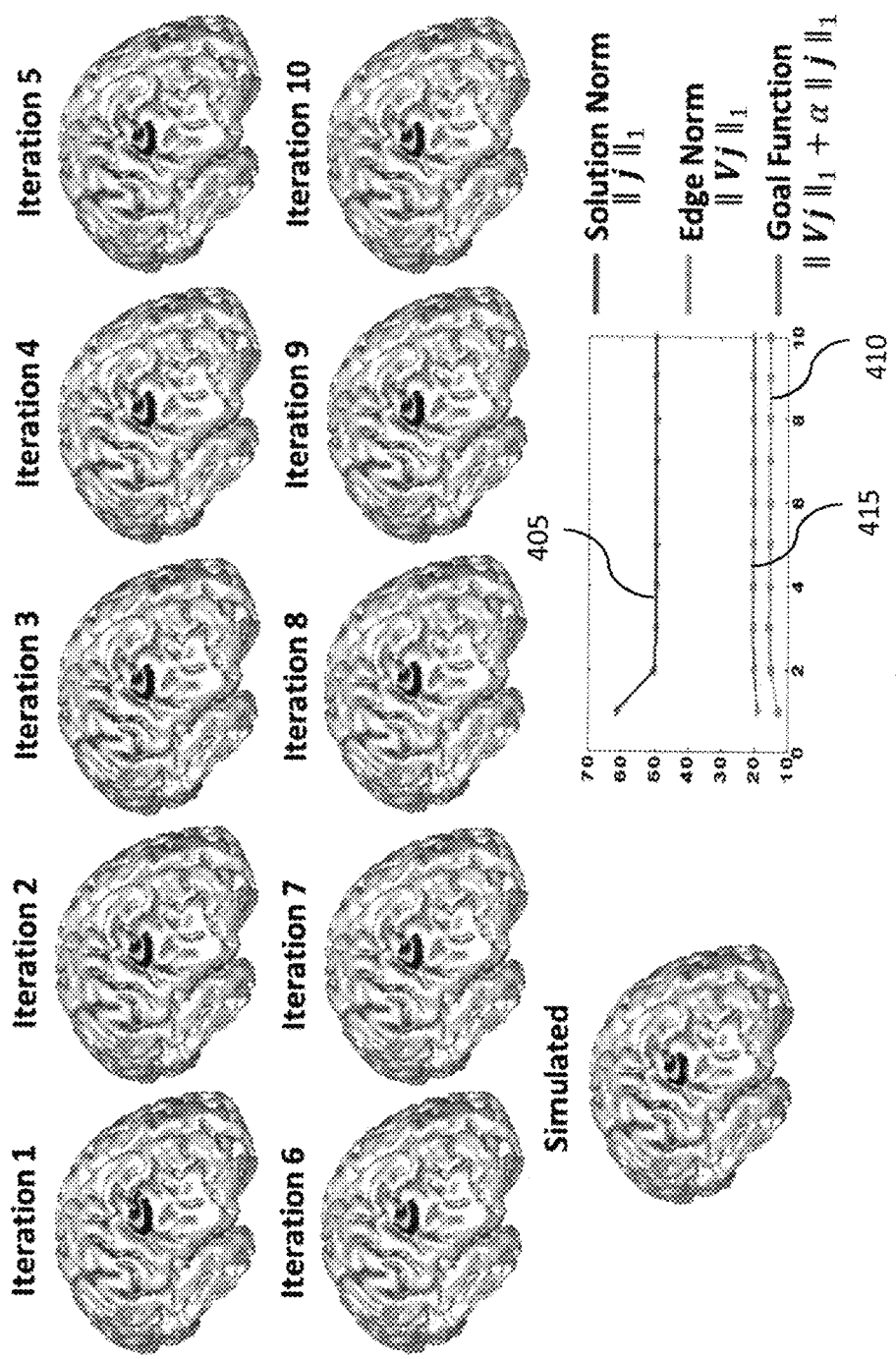
FIG. 4 illustrates the effect of iteration. A 10 mm source is simulated and IRES estimation at each iteration, is depicted. As it can be seen the estimated solution converges to the final solution after a few iterations and more so the continuation of the iterations does not affect the solution (i.e. shrink the solution). The bottom right graph shows the norm of the solution (405) and the gradient of the solution (410) and also the goal function (415) at each iteration. The goal function (penalizing terms) is the term minimized in equation (2).

Another parameter to control for is the number of iterations. In example implementations, iterations continue until the estimation of two consecutive steps do not vary significantly. The actual number of iterations needed may be 2 to 4 iterations, in various implementations. As a result, within a few iterations, an extended solution with distinctive edges from the background activity can be reached. FIG. 4 shows one example. In this case a 10 mm extent source is estimated and the solution is depicted through 10 iterations. As it can be seen, the solution stabilizes after 3 iterations and it stays stable even after 10 iterations. It is also interesting that these iterations do not cause the solution to shrink and produce an overly concentrated solution like the FOCUSS algorithm. This is due to the fact that the regularization term in IRES contains TV and L1 terms which in turn balance between sparsity and edge-sparsity, avoiding overly spread or focused solutions.

In order to form matrix V which approximates some sort of total variation among the dipoles on the cortex, it is important to constitute the concept of neighborhood. Since the cortical surface is triangulated for the purpose of solving the forward problem (using the boundary element model) to form the lead field matrix K, there exists an objective and simple way to define neighboring relationship. The center of each triangle is taken as the location of the dipoles to be estimated (amplitude) and as each triangle is connected to only three other triangles via its edges, each dipole is neighbor to only three other dipoles. Based on this simple relation, neighboring dipoles can be detected and the edge would be defined as the difference between the amplitude of two neighboring dipoles. Based on this explanation one can form matrix V as presented in (4):

$$V = \begin{pmatrix} v_{11} & \cdots & v_{1n} \\ \vdots & \ddots & \vdots \\ v_{T1} & \cdots & v_{Tn} \end{pmatrix} \quad (4)$$

$$\begin{cases} v_{ij} = 1 \text{ and } v_{ik} = -1 & \text{if dipole } j \text{ and } k \text{ are neighbors over edge } i \\ v_{ij} = 0 & \text{otherwise} \end{cases}$$

The number of edges is denoted by T. Basically each row of matrix V corresponds to an edge that is shared between two triangles and the +1 and −1 values within that row are located so as to differentiate the two dipoles that are neighbors over that particular edge. The operator V can be defined regardless of mesh size, as the neighboring elements can be always formed and determined in a triangular tessellation (always three neighbors). However reducing the size of the mesh to very small values (less than 1 mm) is not reasonable as M/EEG recordings are well-known to be responses from ensembles of postsynaptic neuronal activity. Having small mesh grids will increase the size of V relentlessly without any meaningful improvement. On the other hand increasing the grid size to large values (>1 cm) will also give coarse grids that can potentially give coarse results. It is difficult to give a mathematical expression on this but a grid size of 3~4 mm was chosen to avoid too small a grid size and too coarse a tessellation.

Example Implementations—Dynamic Source Imaging with IRES

The example approaches of the present disclosure, iteratively reweighted edge sparsity minimization strategy (IRES), can be used to image the brain electrical activity (or electrical activity of other biological systems/organs, such as the heart) over time and provide a dynamic image of underlying brain activity. One embodiment of the present disclosure is to perform dynamic source imaging as opposed to solving the inverse electromagnetic source imaging (ESI) problem for every time point. The scalp potential (or magnetic field) measurements over the interval to be studied can be decomposed into spatial and temporal components using the independent component analysis (ICA) and/or the principal component analysis (PCA) procedures. In this manner, a temporal basis can be formed for the underlying sources. The underlying electrical activity of the source is modeled as spatial components that have coherent activity over time. In this manner, the brain is decomposed into multiple regions where each region has its specific and coherent activity over time, mathematically speaking:

$$\hat{j}(t) = \Sigma_{i=1}^{N_c} \hat{j}_i \otimes a_i(t) \quad (5)$$

Where $j(t)$ is the underlying electrical activity of the brain over time (an N×T matrix where N is the number of current sources in the brain and T is the number of time points within the time interval of interest in the potential/field recordings), $j_i$ is the activity of a specific region within the brain (an N×1 vector), $i$, with its corresponding activation over time $a_i(t)$ (an 1×T vector). The symbol ⊗ represents an outer product operator. $N_c$ is the number of active regions. If the time-course of underlying sources' activity can be determined from the scalp measurements, then the IRES optimization problem can be solved to determine the $j_i$'s ($j = [j_1, j_2, \ldots]$), as follows:

$$j^L = \operatorname*{argmin}_{j} \sum_{i=1}^{N_c} \|W_{d,i}^{L-1}(Vj_i)\|_1 + \sum_{i=1}^{N_c} \alpha_i \|W_i^{L-1} j_i\|_1 \quad (6)$$

$$\text{subject to } \operatorname{diag}\left\{(\varphi(t) - Kj\mathcal{A})^T \sum\nolimits^{-1} (\varphi(t) - Kj\mathcal{A})\right\} \le \beta$$

where $\varphi(t)$ is the scalp potential (or magnetic field) measurement over the interval of interest (an E×T matrix where E is the number of measurements), K is the lead field matrix (an E×N matrix), $j$ is the unknown current density of the brain regions (an N×$N_c$ matrix), $\mathcal{A}$ is the time course activation matrix (an $N_c$×T matrix) which is given by, $\mathcal{A} = [a_1(t), a_2(t), \ldots]$, $\beta$ is essentially the noise power, to be determined by the discrepancy theorem, $\Sigma$ is the covariance matrix of the noise to be determined from the baseline activity, $W_{d,i}^{L-1}$ and $W_i^{L-1}$ are the weights pertaining to each $j_i$ and are updated with the same rule determined for the IRES, V is the discrete gradient operator, $\alpha_i$ are hyperparameters balancing between the two terms in the regularization terms (pertaining to each $j_i$) which will be tuned using the L-curve approach and L is counting the iteration steps. The component analysis will be used to estimate the $a_i(t)$'s (and consequently $\mathcal{A}$) as there is a linear relation between underlying current density distribution $j$ anf the scalp potential/field measurements $\varphi$:

$$\varphi(t) = Kj(t) = K \sum_{i=1}^{N_c} j_i \otimes a_i(t) = \sum_{i=1}^{N_c} (Kj_i) \otimes a_i(t) = \sum_{i=1}^{N_c} \psi_i \otimes a_i(t) \quad (7)$$

Where $\psi_i = K j_i$. Thus, if the scalp measurements can be decomposed into spatio-temporal components $\varphi(t) = \sum_{i=1}^{N_c} \varphi_i \otimes a_i^*(t)$, the time-course activity of underlying sources can be extracted, in the brain, although the decomposed temporal components $a_i^*(t)$ might not be equal to $a_i(t)$ in a one-to-one manner, as long as $\mathcal{A}^* = [a_1^*(t), a_2^*(t), \ldots]$ contains the same essential components of $\mathcal{A}$, or $$\mathcal{A} = \mathcal{L}\{\mathcal{A}^*\} = L\mathcal{A}^* \quad (8)$$

Where $\mathcal{L}$ is a linear transformation between the two matrices (L is an $N_c \times N_c$ square matrix). The number of components cannot be determined a priori, but there are two methods to accomplish this goal. One, is to discard components which are noisy and extremely weak not surpassing the noise level (which can be computed from baseline activity in the measurements). The second approach would be to select components that are either time-locked to the stimuli present in our experiment (external stimuli such as a flash of light in case of visual evoked responses or internal stimuli such as inter-ictal spike activity or the onset of seizure activity) or to select components which present desirable features in the spectrum such as event related synchronization (ERS) and event related desynchronization (ERD). In any case, PCA and ICA are used extensively in separating desirable and noisy signals, in the signal processing applications and thus provide a powerful framework to estimate $\mathcal{A}$ or the temporal basis. It is good to note that the disclosed formulation still estimates $j_i$'s, inverting the effects of volume conduction, as the spatial component is affected by the volume conduction, while the temporal activity, which is not affected by the volume conduction, is estimated from the scalp measurements. The disclosed method could also be applied iteratively, to increase accuracy; that is, after the locations and time-course activity of the underlying sources are estimated, the time course activity of each $j_i$ can be estimated by projecting the scalp measurements to the columns of K pertaining to source locations in the estimated $j_i$ to estimate the corresponding $a_i(t)$, and then once the temporal basis is formed again, the process of estimating $j_i$'s can be repeated. In this manner, the spatio-temporal source imaging IRES can improve at every iteration.

Example Implementations—Fast Implementation of Dynamic Source Imaging with IRES

An efficient algorithm can be used to implement IRES in a manner suitable for tracking dynamic brain signals with fast variations over time. As discussed above, in order to solve the problem efficiently it may be assumed that extended sources with coherent activity over the extended source patch are generating the EEG or MEG signal, in a given time window.

Based on convex optimization, namely the fast iterative shrinkage-thresholding algorithm (FISTA), the spatio-temporal IRES can be implemented in the following algorithm. In this algorithm, after a time basis function is estimated from surface measurements such as EEG and/or MEG, the underlying extended source generating these signals will be estimated. Basically, in these embodiments, the following optimization problem is solved at each iteration:

$$j^L = \operatorname*{argmin}_{j} \sum_{i=1}^{N_c} \|W_{d,i}^{L-1}(Vj_i)\|_1 + \sum_{i=1}^{N_c} \alpha_i \|W_i^{L-1} j_i\|_1 \quad (9)$$

$$\text{subject to } \|\varphi(t) - K j \mathcal{A}\|_F^2 \le \beta$$

Where $\varphi(t)$ is the scalp electrical/magnetic measurement over the interval of interest (an E×T matrix where E is the number of measurements and T is the number of time points), K is the lead field matrix (an E×N matrix), $j$ is the unknown current density of the focal brain regions (an N×$N_c$ matrix), $\mathcal{A}$ is the time course activation matrix (an $N_c$×T matrix) which is given by, $\mathcal{A} = [a_1(t), a_2(t), \ldots]$, $\beta$ is essentially the noise power, to be determined by the discrepancy theorem and the data is assumed to be pre-whitened using the noise covariance estimated from baseline, $W_{d,i}^{L-1}$ and $W_i^{L-1}$ are the weights pertaining to each $j_i$ and are updated with the same rule determined for the IRES, V is the discrete gradient operator, $\alpha_i$ are hyperparameters balancing between the two terms in the regularization terms (pertaining to each $j_i$) which will be tuned using the L-curve approach (as discussed for the IRES) and L is counting the iteration steps.

Previously we have discussed how the iterations can improve estimates at every step and how to update the weights at every iteration, how to find β and determine α, and how to determine $\mathcal{A}$ using component analysis or time-frequency methods such as wavelet analysis; what we will discuss here is how to solve the basic problem of the following form which is the backbone for solving the IRES problem in various embodiments of the disclosure:

$$\hat{j} = \operatorname*{argmin}_{j} \|\mathcal{W}_d \odot (V j)\|_1 + \alpha \|\mathcal{W} \odot j\|_1 \quad (10)$$
$$\text{subject to } \|\varphi(t) - K j \mathcal{A}\|_F^2 \le \beta$$

In this formulation all the $\mathcal{W}_{d,i}$ and $\mathcal{W}_i$ are concatenated into matrices of the same size as $V j$ and $j$ respectively; noting that the weight matrices are diagonal matrices, they can be narrowed down to column vectors without loss of data (diagonal elements of the matrix) and subsequently concatenated together to form a matrix of corresponding sizes to $V j$ and $j$. The operator $\odot$ denotes an element-by-element matrix multiplication.

Example implementations of this problem use augmented Lagrangian methods; that is to separate variables relating to the current density $j$ and edge variables $V j$, in order to solve the problem in (10) efficiently using block-coordinate descent algorithms. Re-writing the problem in (10) in its equivalent following form:

$$\hat{j} = \operatorname*{argmin}_{j} \|\mathcal{W}_d \odot \mathcal{Y}\|_1 + \alpha \|\odot j\|_1 \quad (11)$$
$$\text{subject to } \|\varphi(t) - K j \mathcal{A}\|_F^2 \le \beta$$
$$\mathcal{Y} = V j$$

And then using the augmented Lagrangian approach, solved the following modified problem which is not only equivalent to solving (11) but also a separable and strictly convex optimization problem, which can be solved efficiently using existing convex optimization problems:

$$\hat{j} = \operatorname*{argmin}_{j} \|\mathcal{W}_d \odot \mathcal{Y}\|_1 + \alpha \|\mathcal{W} \odot j\|_1 + \frac{\lambda}{2} \|\mathcal{Y} - V j\|_F^2 \quad (12)$$
$$\text{subject to } \|\varphi(t) - K j \mathcal{A}\|_F^2 \le \beta$$

Where λ is a smoothing hyper-parameter which can be tuned from data easily. In order to solve the problem in (12), a block coordinate approach is followed, where $j$ is updated (estimated) first, assuming that $\mathcal{Y}$ is given, then once $j$ is estimated (updated) $\mathcal{Y}$ will be updated based on the recently estimated $j$, at the next iteration. This alternation will continue until the solution converges to a fixed point, i.e. $j$ and $\mathcal{Y}$ do not vary much at successive iterations and converge to a solution. It is proven in convex optimization theory that such a strictly convex optimization problem under relatively achievable mathematical conditions will converge to the optimal solution regardless of initiation. Basically the problem disclosed in (12) can be solved in the following manner; by solving the following sub-problems:

Problem S1:

$$j^{K+1} = \operatorname*{argmin}_{j} \alpha \|\mathcal{W} \odot j\|_1 + \frac{\lambda}{2} \|\mathcal{Y}^K - V j\|_F^2 = \quad (13)$$
$$\operatorname*{argmin}_{j} \|\mathcal{W} \odot j\|_1 + \frac{\lambda}{2\alpha} \|\mathcal{Y}^K - V j\|_F^2$$
$$\text{subject to } \|\varphi(t) - K j \mathcal{A}\|_F^2 \le \beta$$

Problem S2:

$$\mathcal{Y}^{K+1} = \operatorname*{argmin}_{j} \|\mathcal{W}_d \odot \mathcal{Y}\|_1 + \frac{\lambda}{2} \|\mathcal{Y} - V j^{K+1}\|_F^2 \quad (14)$$
$$\text{subject to } \|\varphi(t) - K j^{K+1} \mathcal{A}\|_F^2 \le \beta$$

But given that the condition $\|\varphi(t) - K j^{K+1} \mathcal{A}\|_F^2 \le \beta$ is already satisfied in the previous succession in (13) in solving problem S1, problem S2 is really an unconstrained optimization problem as follows:

Problem S2:

$$\mathcal{Y}^{K+1} = \operatorname*{argmin}_{j} \|\mathcal{W}_d \odot \mathcal{Y}\|_1 + \frac{\lambda}{2} \|\mathcal{Y} - V j^{K+1}\|_F^2 \quad (15)$$

Thus sub-problems S1 and S2 will have to be solved in succession to solve the problem disclosed in (10). The sub-problems S1 and S2 can readily be solved by, for example, adopting a modified fast iterative shrinkage thresholding algorithm (FISTA) algorithm. The modification is in implementing the hyper-ellipsoid constraint of our problem or the noise constraint, $\|\varphi(t) - K j^{K+1} \mathcal{A}\|_F^2 \le \beta$. This constraint basically states that any solution obtained for problems S1 and S2 that minimizes the goal functions, must also satisfy the constraint; geometrically speaking the solution must fall within the hyper-ellipsoid. This means that any solutions obtained that minimizes the goal functions of S1 must then be projected to the boundary (hyper-surface) of this hyper-ellipsoid. This means that for a given $j_o$ that say minimizes problem S1, the correction vector $\delta_j$ has to be found such that $\widehat{j_o} = \mathcal{P}_{\hat{\beta}}(j_o) = j_o + \delta_j$ falls within the hyper-ellipsoid ($\mathcal{P}_{\hat{\beta}}(\ )$ denotes the projection operator). Mathematically speaking the projection problem can be described (formulated) as follows:

Problem P:

$$\delta_j = \operatorname*{argmin}_{\delta_j} \|\delta_j \mathcal{A}\|_F^2 \quad (16)$$
$$\text{subject to } \|\varphi(t) - K(j_o + \delta_j)\mathcal{A}\|_F^2 \le \beta$$

Or equivalently if denoting by $\hat{\varphi} = \varphi(t) - K j_o$ and by $\hat{\beta} = T\beta$; then (16) can be reformulated into the following form which is basically a minimum norm estimation problem and can be solved by differentiating the Lagrangian and setting its derivative equal to zero, which yields closed-form solutions for problem P. This means that the projection which is an essential step and has to be performed at every step of solving problem S1, can be solved efficiently:

Problem P:

$$\hat{\delta}_j = \underset{\delta_j}{\operatorname{argmin}} \|\delta_j \mathcal{A}\|_F^2 \quad (17)$$

$$\text{subject to } \|\hat{\varphi} - K\delta_j \mathcal{A}\|_F^2 \leq \hat{\beta}$$

Figure 5:
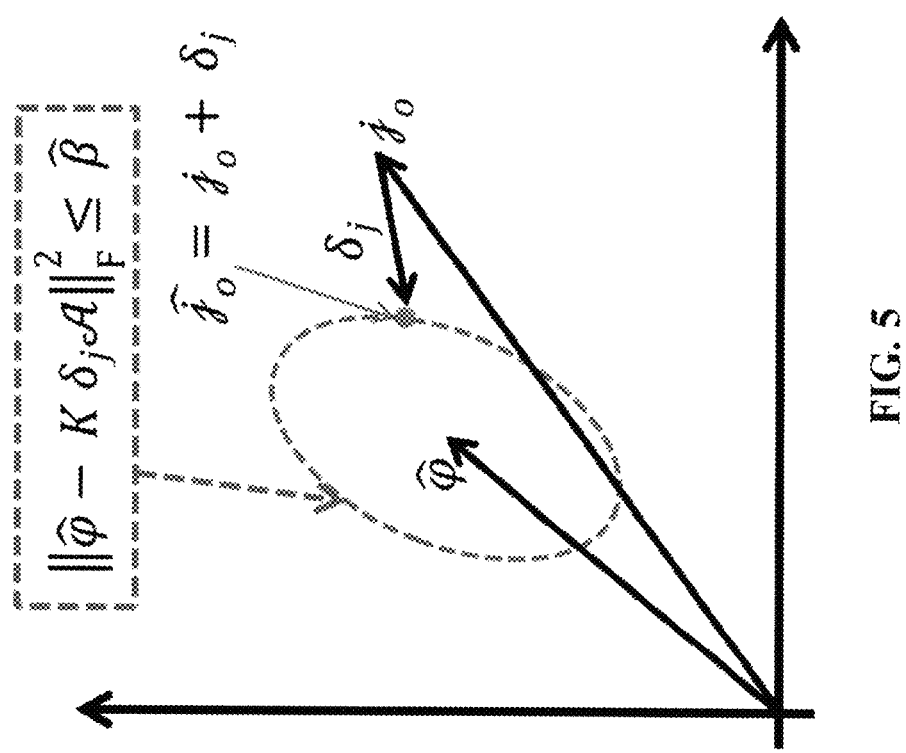
FIG. 5 illustrates projecting to a hyper-ellipsoid surface. The role of the constraint and how hyper-ellipsoid surface projection works are schematically shown.

This is schematically shown in FIG. 5. The closed form solution to problem P is as follows:
Problem P:

$$\hat{\delta}_j = \lambda^* \mathcal{K}^T (I + \lambda^* \mathcal{K}\mathcal{K}^T)^{-1} \hat{\varphi} \mathcal{A}^T (\mathcal{A}\mathcal{A}^T)^{-1} \quad (18)$$

Where $\lambda^*$ is a scalar which is calculated by solving the following problem (which can be readily solved numerically using Newton's method):

$$\sum_{i=1}^E \frac{\sum_t \varphi_r(i,t)^2}{(1 + \lambda^* d_{ii})^2} = \hat{\beta} \quad (19)$$

Where $d_{ii}$ are diagonal elements of matrix $\mathcal{D}$ and $\varphi_r = \mathcal{U} \hat{\varphi} \mathcal{A}^T (\mathcal{A}\mathcal{A}^T)^{-1} \mathcal{A}\mathcal{D}\mathcal{U}\mathcal{K}\mathcal{K}^T \mathcal{K}\mathcal{K}^T = \mathcal{U}^T\mathcal{D}\mathcal{U}$ Solving problem S1 and S2 is trickier as there is a norm-1 term in the goal function which is non-differential; however these problems can be solved easily (as demonstrated in the convex optimization problem literature) using the soft threshold operator which is defined as follows:

$$\mathcal{T}_\eta(x) = \begin{cases} x - \eta & \text{if } x \geq \eta \\ 0 & \text{if } -\eta \leq x \leq \eta \\ x + \eta & \text{if } x \leq -\eta \end{cases} \quad (20)$$

Where $\eta$ is a positive number. The solution to an unconstrained minimization problem like problem S2 is the following (performing simple partitioning and then differentiating the goal function):

$$\mathcal{Y}^{K+1} = \underset{\mathcal{J}}{\operatorname{argmin}} \|\mathcal{W}_d \odot \mathcal{Y}\|_1 + \frac{\lambda}{2}\|\mathcal{Y} - V\mathcal{J}^{K+1}\|_F^2 = \mathcal{T}_{\frac{w_d}{\lambda}}(V\mathcal{J}^{K+1}) \quad (21)$$

Where $w_d$ denotes the corresponding element of $\mathcal{W}_d$ and $\mathcal{Y}$. Solving problem S1 might seems more difficult compared to S2, as there is a constraint to satisfy, but based on simple principles from optimization theory, the constraint can be assumed not to present, thus to solve the problem and subsequently project the solution to the hyper-ellipsoid to satisfy the constraint (solving problem P for the obtained solution). Again following simple partitioning, differentiating and projecting the solution to the hyper-ellipsoid, problem S1 is solved as follows:

$$\mathcal{J}^{K+1} = \underset{\mathcal{J}}{\operatorname{argmin}} \|\mathcal{W} \odot \mathcal{J}\|_1 + \frac{\lambda}{2}\|\mathcal{Y}^K - V\mathcal{J}\|_F^2 \quad (22)$$

$$= \mathcal{P}_{\hat{\beta}}\left(\mathcal{T}_{\frac{\alpha \cdot w}{\lambda \cdot \mathcal{L}_v}}\left(\tilde{\mathcal{J}}^K - \frac{1}{\mathcal{L}_v}(V^TV\tilde{\mathcal{J}}^K - (V^T\mathcal{Y}^K))\right)\right)$$

Where $w$ corresponds to the corresponding elements of $\mathcal{W}$ in the $\mathcal{J}$, and $\mathcal{L}_v$ is the Lipschitz constant of the function $f(x) = V^TVx$ or basically the largest eigenvalue of $V^TV$. Thus all the sub-problems, S1, S2 and P can be solved efficiently and easily. The FISTA algorithm has a method for the updating rule of the variables that should be updated at each iteration K (this is the internal iterations of the problem and not to be confused with outer iterations where the weights are updated). Putting together the solutions obtained for problem S1 (22), problem S2 (21) and the projection problem P (18-19), the following algorithm is proposed to solve the optimization problem disclosed in (12) (spatio-temporal IRES):

1. Initialize with $t_1 = 1$, $\tilde{\mathcal{J}}^1 = \mathcal{J}^0 = 0$, $\mathcal{Y} = V\tilde{\mathcal{J}}^1 = 0$.

2. $\mathcal{J}^K = \mathcal{P}_{\hat{\beta}}\left(\mathcal{T}_{\frac{\alpha \cdot w}{\lambda \cdot \mathcal{L}_v}}\left(\tilde{\mathcal{J}}^K - \frac{1}{\mathcal{L}_v}(V^TV\tilde{\mathcal{J}}^K - (V^T\mathcal{Y}^K))\right)\right)$ $$t_{K+1} = \frac{1 + \sqrt{1 + 4t_K^2}}{2}$$

$$\tilde{\mathcal{J}}^{K+1} = \mathcal{J}^K + \left(\frac{t_K - 1}{t_{K+1}}\right) \cdot (\mathcal{J}^K - \mathcal{J}^{K-1})$$

3. $\mathcal{Y}^K = \mathcal{T}_{\frac{w_d}{\lambda}}(V\mathcal{J}^{K+1}\tilde{\mathcal{J}}^{K+1})$ 4. Continue steps 2 and 3 at every iteration until we converge to a solution where $\mathcal{J}$ stabilizes and converges.

These example steps outlined above will solve the spatio-temporal IRES formulated in (12). As it can be seen, all steps are not computationally demanding and are efficient to perform and thus the algorithm is efficient and fast. The introduction and use of the update rule parameter, $t$, and the intermediate variable $\tilde{\mathcal{J}}$ at each iteration, is based on the FISTA algorithm. This algorithm will be faster than simply updating the variables and thus converges to the optimal solution much faster than conventional methods and algorithms. The disclosed FAST-IRES is fast and can be solved in a matter of seconds for problems normally coming across in EEG/MEG source imaging; that is usually data intervals of lengths which are in the order of seconds (T~3000 samples or more) and realistic problem sizes with couple of hundreds of electrodes/sensors (E~100-200 measurements) and tens of thousands of unknowns (N~10000-20000 variables or length of $\mathcal{J}$) for numerous temporal components ($N_c$~10).

The FAST-IRES algorithm can be used for any source imaging problem to monitor the underlying and highly dynamic brain activities using non-invasive surface measurements. This can specifically be useful in identifying the location, extent and dynamics of seizures in patients with epilepsy to help guide for surgical resection of the epileptogenic zone or electrical grid placement, in medically intractable epilepsy patients or for basic science where the epilepsy networks can be studied non-invasively.

Figure 6:
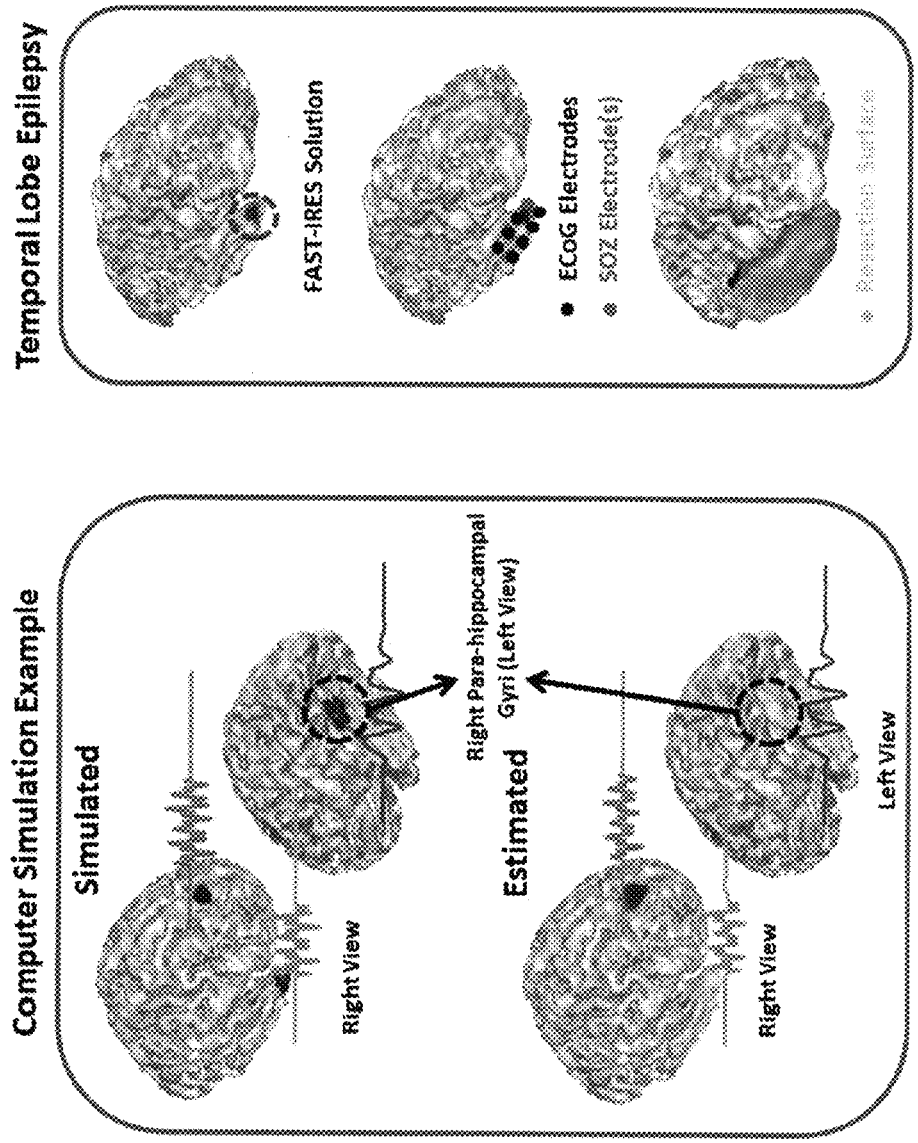
FIG. 6 illustrates FAST-IRES application to simulation data and clinical epilepsy data. The left panel shows the computer simulation results where three sources with corresponding time courses were simulated and subsequently the location, extent and the time-course of activity of these sources were estimated using the FAST-IRES algorithm. The right panel shows the application of the algorithm to a temporal lobe epilepsy patient who became seizure-free after surgical resection of the right temporal lobe. The solution is compared to clinical findings such as the seizure onset zone (SOZ) determined from invasive intra-cranial EEG and the resection surface obtained from post-operative magnetic resonance imaging (MRI) images. The FAST-IRES imaging results are in full accord with clinical findings based on invasive recordings and surgical outcome.

FIG. 6 depicts the application of FAST-IRES in a computer simulation example as well as real epilepsy patient. As the example indicates, FAST-IRES is successful in efficiently and accurately determining the underlying brain networks. As mentioned previously, imaging epilepsy networks is only one application of this algorithm and potentially any spatio-temporal underlying brain activity can be monitored using the disclosed FATS-IRES algorithm.

Example Computer Simulation Protocol

In order to analyze IRES performance, a series of computer simulations were conducted in a realistic cortex model.

The cortex model was derived from MR images of a human subject. The MR images were segmented into three layers, namely the brain tissue, the skull and the skin. Based on this segmentation a three layer BEM model was derived to solve the forward problem and obtain the lead field matrix, constituting the relation between current density dipoles and the scalp potential. The conductivity of the three layers, i.e. brain, skull and skin, were selected respectively as 0.33 S/m, 0.0165 S/m and 0.33 S/m. The number of recording electrodes used in the simulation is 128 channels. 100 random locations on the cortex were selected and at each location sources with different extent sizes were simulated, ranging from 10 mm to 30 mm in radius size. The amplitude of the dipoles were set to unity, so the cortical surface was partitioned into active (underlying source) and non-active (not included within the source) area. The orientation of the sources were taken to be normal to the cortical surface, as the pyramidal cells located in the gray matter responsible for generating the EEG signals are oriented orthogonal to the cortical surface. The orientation of the dipoles was accordingly fixed when solving the inverse problem. Different levels of white Gaussian noise were added to the generated scalp potential maps to make simulation more realistic. The noise power was controlled to obtain different levels of desired signal to noise ratio (SNR), namely 10 dB and 20 dB (another set of simulations with 6 dB SNR was also conducted as explained in the next paragraph). These SNR values are realistic in many applications including epileptic source imaging. The inverse solutions were obtained using IRES and the estimated solutions were compared to the ground truth (simulated sources) for further assessment. The results of these simulations are presented in FIGS. 7 to 9.

Figure 7:
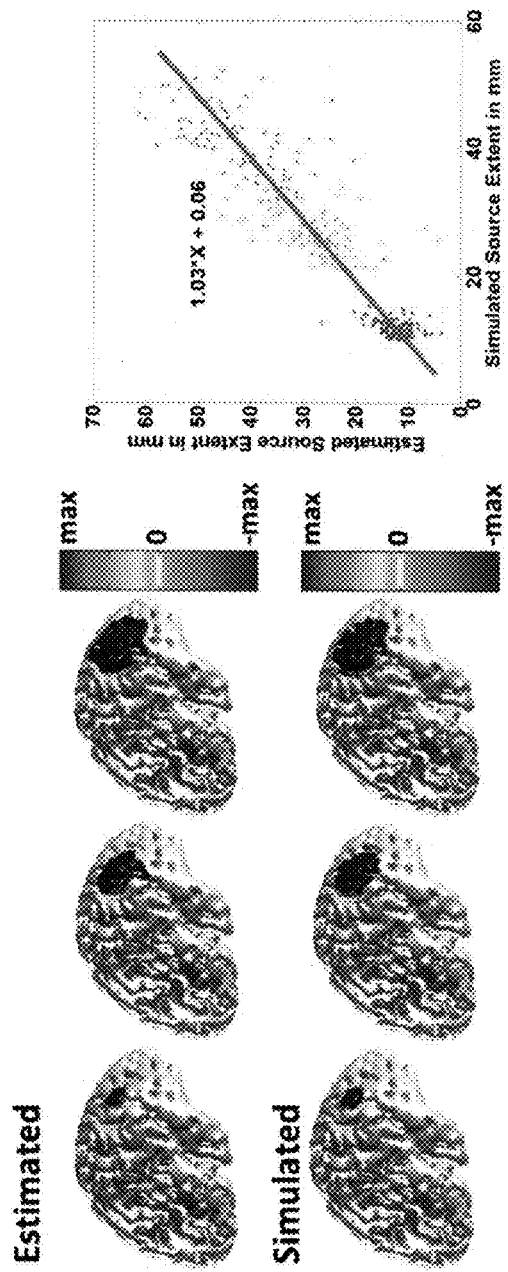
FIG. 7 provides example simulation results. In the left panel three different source sizes were simulated with extents of 10 mm, 20 mm and 30 mm (lower row). White Gaussian noise was added and the inverse problem was solved using the disclosed IRES method. The results are shown in the top row. The same procedure was repeated for random locations over the cortex. The extent of the estimated source is compared to that of the simulated source in the right panel. The signal-to-noise ratio (SNR) is 20 dB.
Figure 8:
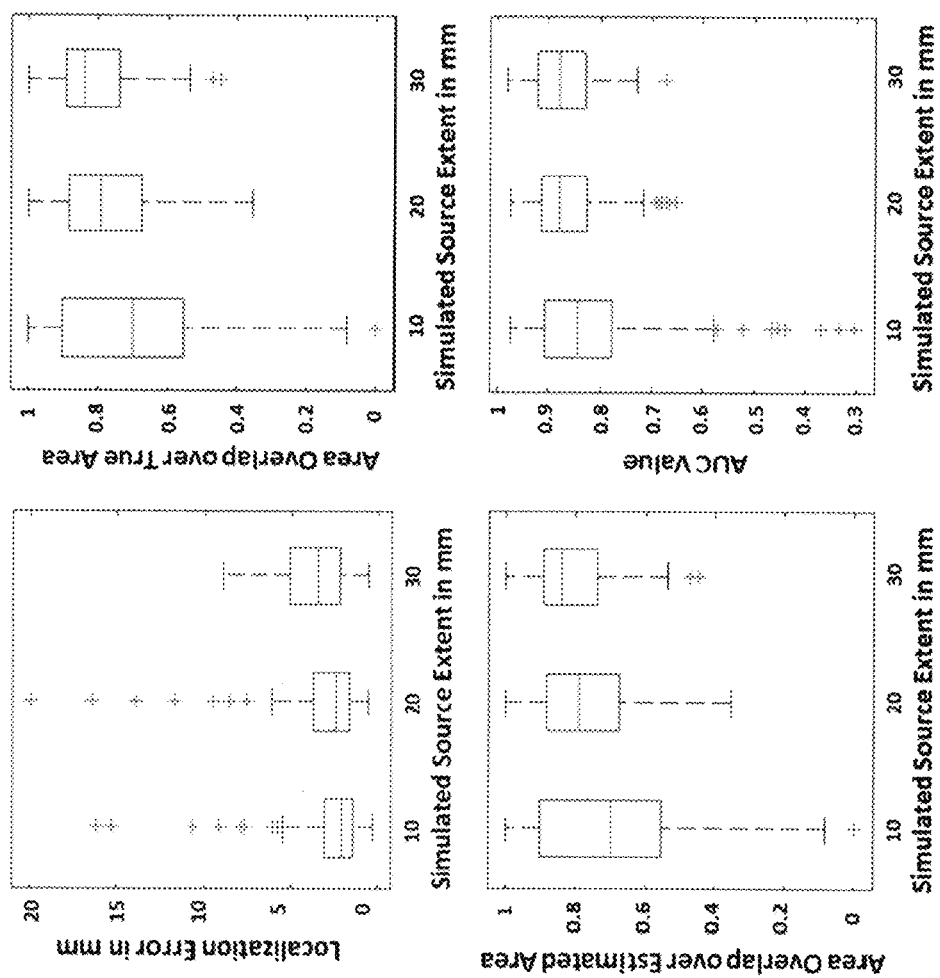
FIG. 8 provides simulation statistics. The performance of the simulation study is quantified using the following measures, localization error (upper left), area under curve (AUC) (upper right) and the ratio of the area of the overlap between the estimated and true source to either the area of the true source or the area of the estimated source (lower row). The SNR is 20 dB in this study. The simulated sources are roughly categorized as small, medium and large with average radius sizes of 10 mm, 20 mm and 30 mm, respectively. The localization error (LE), AUC and normalized overlap ratio (NOR) are then calculated for the sources within each of these classes. The boxplots show the distribution of each metric to provide a brief statistical review of the distribution of these metrics for all of the data. The metrics and how to interpret them are further discussed below in relation to methods used.
Figure 9:
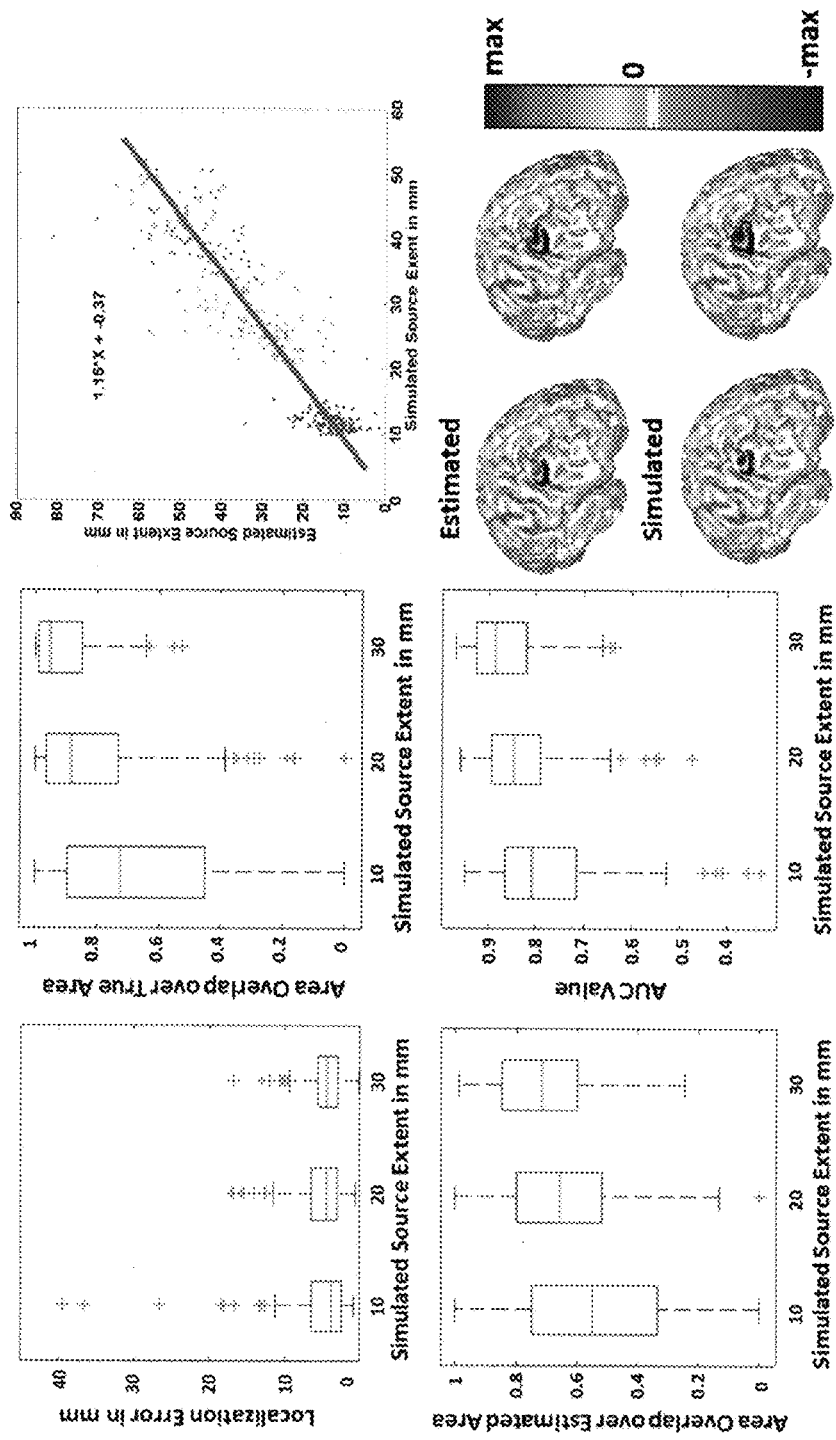
FIG. 9 illustrates simulation statistics and performance of the simulation study when the SNR is 10 dB. Results are quantified using the following measures, localization error, AUC and the ratio of the area of the overlap between the estimated and true source to either the area of the true source or the area of the estimated source. The statistics are shown in the left panel. In the right panel, the relation between the extent of the estimated and simulated source is delineated (top row). Two different source sizes namely, 10 mm and 15 mm, were simulated and the results are depicted in the right panel (bottom row).

In order to compare the effect of modeling parameters on the inverse algorithm, another series of simulations were also conducted for which the forward and inverse model was different (in addition to the previous results presented in FIGS. 7 to 9). The mesh used for the forward problem was very fine with 1 mm spacing consisting of 225,879 elements on the cortex. A BEM model consisting of three layers, i.e. brain, skull and skin with conductivities of 0.33 S/m, 0.015 S/m and 0.33 S/m was used for the forward model. For the inverse model a coarse mesh of 3 mm spacing consisting of 28,042 elements was used. The inverse BEM model consists of three layers, i.e. brain, skull and skin with conductivities of 0.33 S/m, 0.0165 S/m and 0.33 S/m. Basically the conductivity ratio is changed by 10% in the inverse model compared to the forward model and also a different and much finer grid is used for the forward model in comparison to the inverse model. In this manner the dependency of IRES performance is reduced to modeling parameters such as grid size and conductivity values (by using different lead field matrices for forward and inverse). In addition to that, realistic noise recorded from a human subject was used as the additive noise so as to avoid using only white noise. Low SNR of 5~6 dB was also tested following, to make sure IRES can be used in noisier conditions. The results of these simulations are presented in FIG. 10 and FIG. 11.

To further assess the effect of slight differences in conductivities on inverse algorithms' performance, another inverse model was formed and used as well. This inverse model is the same as the inverse model described in the previous paragraph, meaning that in these simulations the grids used for the forward and inverse model were different but the conductivity values were not. The results of the simulations are presented in FIG. 12 and FIG. 13.

Figure 21:
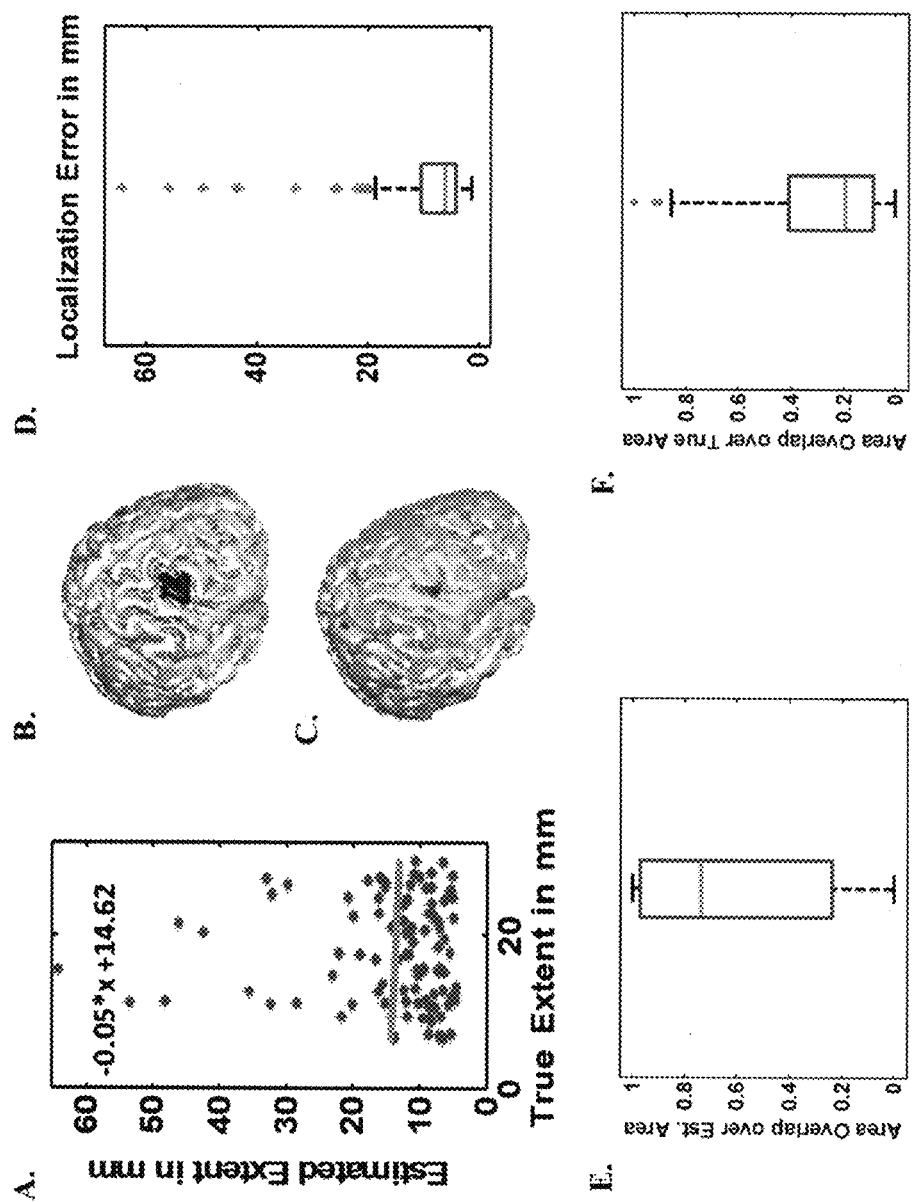
FIG. 21 provides Monte Carlo simulations for the differing BEM models at 6 dB SNR (cLORETA). The estimated source extent is graphed against the true (simulated source) extent (A). An example of the target (true) source (B) and its estimated source using the cLORETA algorithm (C). The localization Error (D), Normalized overlaps defined as overlap area over estimated source area (E) and overlap area over true source area (F), are presented in this figure. A 50% thresholding is applied (all data). The boxplots show the distribution of each metric to provide a brief statistical review of the distribution of these metrics for all of the data. The metrics and how to interpret them are further discussed below in relation to methods used.
Figure 22:
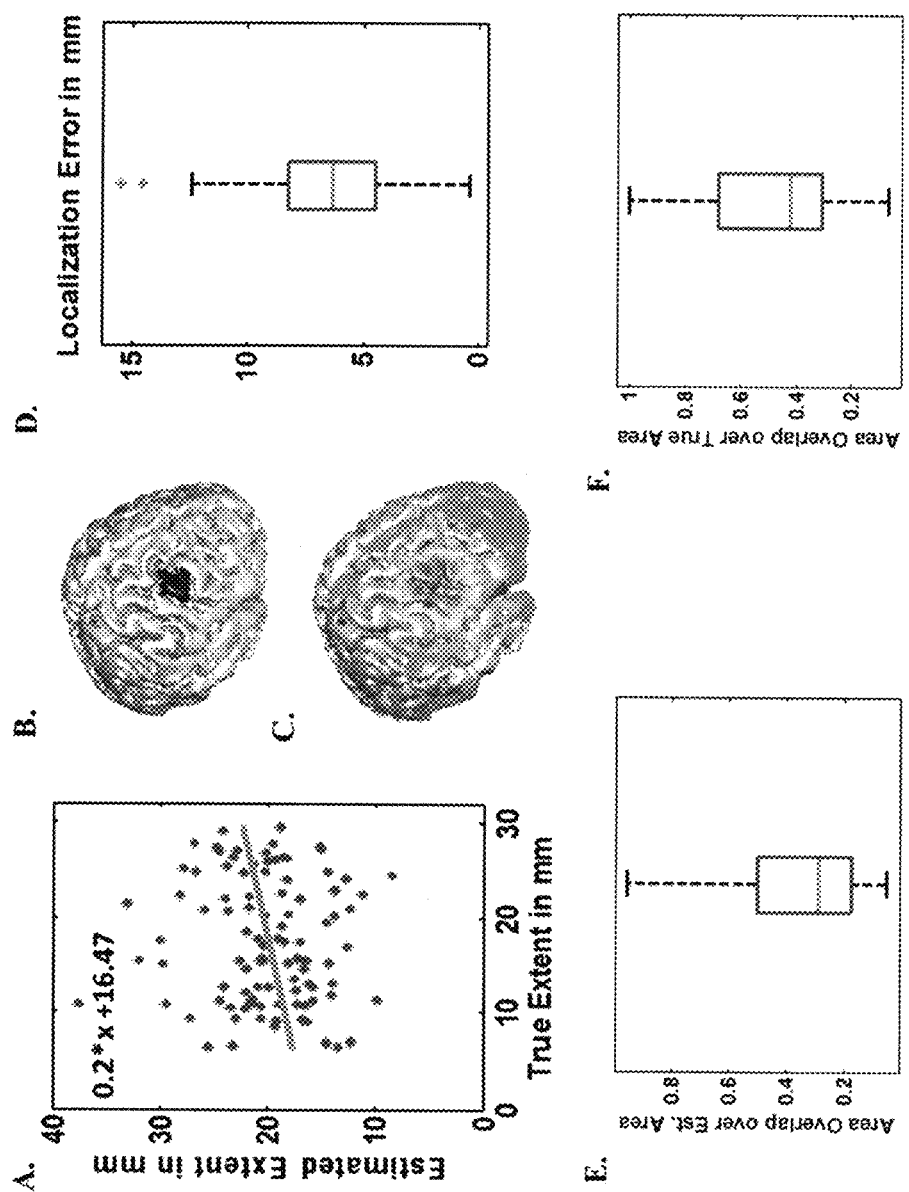
FIG. 22 provides Monte Carlo simulations for the differing BEM models at 6 dB SNR (FVR). The estimated source extent is graphed against the true (simulated source) extent (A). An example of the target (true) source (B) and its estimated source using the FVR algorithm (C). The localization Error (D), Normalized overlaps defined as overlap area over estimated source area (E) and overlap area over true source area (F), are presented in this figure. A 50% thresholding is applied (all data). The boxplots show the distribution of each metric to provide a brief statistical review of the distribution of these metrics for all of the data. The metrics and how to interpret them are further discussed below in relation to methods used.

Model violations such as non-constant sources (amplitude) and multiple simultaneous active sources were also tested. Additionally cLORETA and focal vector field reconstruction (FVR) were used to estimate solutions and the results from these inverse algorithms were compared with IRES (these results are presented in FIGS. 21 and 22).

To further evaluate the performance of IRES non-constant sources (for which the dipoles within the source patch did not have constant amplitudes and varied in amplitude) and multiple simultaneously active sources were also simulated and tested. Results of IRES performance are presented in FIG. 14 for multiple cases in these scenarios. More detailed results and analyses are presented in FIGS. 23 to 26.

Example Performance Measures

In order to evaluate IRES performance, multiple metrics were used. As extended sources are being considered in this study, appropriate metrics being able to compare extended sources should be used. The first measure is the localization error (LE). The localization error calculates the Euclidean distance between the center of mass of the simulated and estimated sources. In order to compare the shape and relative position of the estimated and simulated sources the overlap metric is used. The amount of overlap between the estimated and simulated sources is calculated and divided by either the simulated source area or the estimated source area to derive a normalized overlap ratio (NOR). This normalized overlap shows how well the two distributions match each other. These measures should both be as close as possible to 1. If an overestimated or underestimated solution is obtained, one of the two measures can be close to 1 while the other decreases significantly. Another important measure is the area under curve (AUC) analysis. The curve mentioned is the receiver operating characteristics (ROC) curve. The AUC enables us to compare two source distributions (one is the estimated source distribution and the other one is the simulated source). The closer this AUC value is to 1, the better our estimation of the simulated source will be.

Example Clinical Testing

Figure 15:
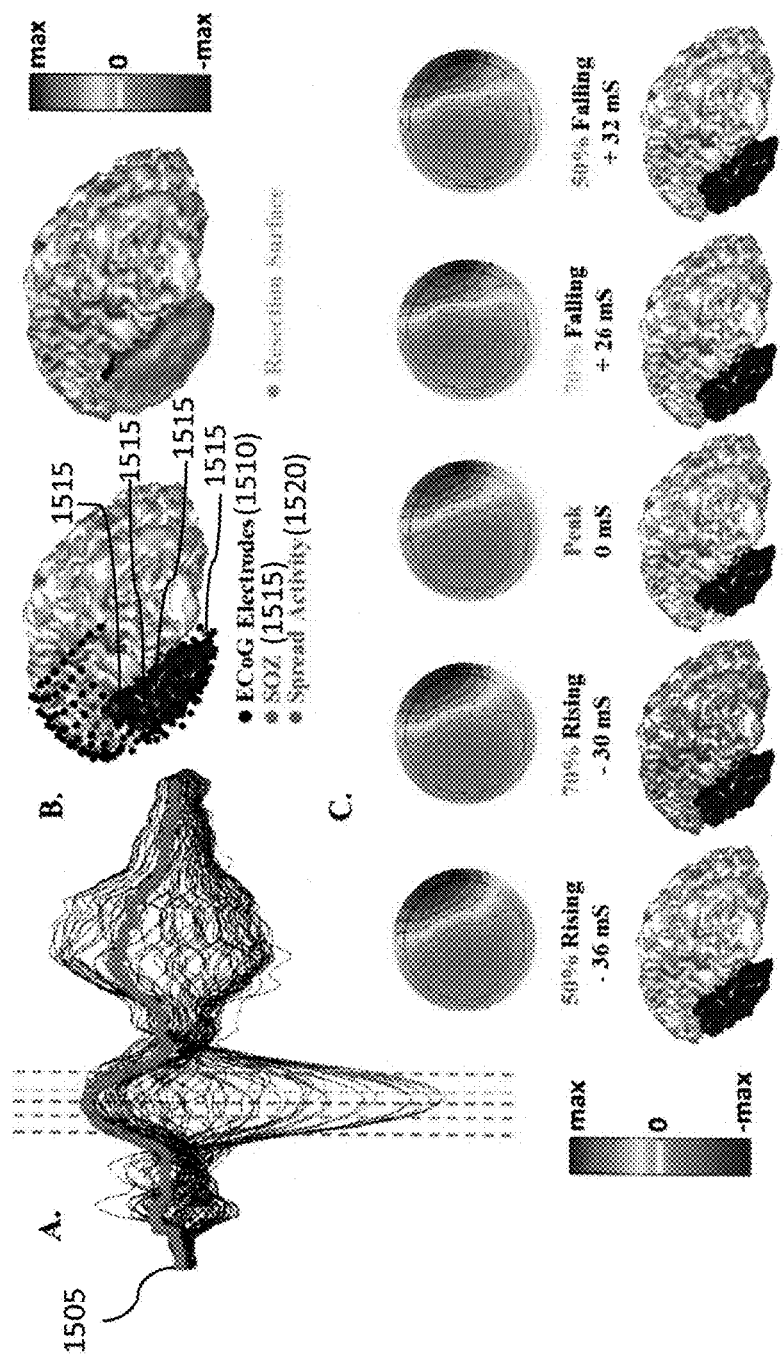
FIG. 15 illustrates source extent estimation results in a patient with temporal lobe epilepsy. (A) Scalp EEG waveforms of the inter-ictal spike in butterfly plot on top of the mean global field power (trace 1505). (B) The estimated solution at Peak time (by Vector-based IRES (VIRES)) is shown on top of the ECoG electrodes and SOZ (left) and the surgical resection (right). (C) Scalp potential maps and estimation results of source extent at different latency of the interictal spike.

In order to determine if IRES could be used in practical settings and ultimately translated into clinical settings, the proposed algorithm was also tested in patients suffering from partial (focal) epilepsy. Three patients underwent surgery and were seizure free at one year post-operation follow-up. Two of the patients also had intracranial EEG recordings (before surgery) from which the seizure onset zone (SOZ) and spread activity electrodes were determined (FIG. 15). All patients had pre-surgical MRI as well as post-surgical MRI images (an example of pre/post-surgical MRI images is presented in FIG. 16). The pre-surgical MRI was used to form individual realistic geometry head models, i.e. BEM models, for every patient. The BEM model composed of three layers. The conductivity of the three layers, i.e. brain, skull and skin, were selected respectively as 0.33 S/m, 0.0165 S/m and 0.33 S/m. The post-op MRI was used to locate and segment the surgical resection to later compare with IRES estimated solution. The EEG recordings were filtered with a band-pass filter with cut-off frequencies set at 1 Hz and 50 Hz. The spikes were averaged around the peak of their mean global field power (MGFP) to produce a single averaged spike; on average 10 spikes were averaged for this study. These averaged spikes were then used for further source imaging analysis. The electrode montage used for these patients contained 76 electrodes and the electrode locations were digitized and used in the inverse calculation.

The estimated solution by IRES is compared to the surgical resection surface and SOZ whenever available.

The cortical surface was triangulated into 1 mm and 3 mm mesh for the computer simulations and clinical data analysis. In order to solve the SOCP problem, a convex problem solver called CVX was used. CVX contains many solvers including the self-dual-minimization (SeDuMi) which is a MATLAB (Mathworks, Natick, Mass.) compatible package implementing an interior path method (IPM) for solving the SOCP problems. It takes about 2-4 minutes to solve (3) at each iteration on widely available desktop computers (3.4 GHz CPU and 4 Gbytes RAM). Although such a computation time is about 20 times that of MN-like algorithms, it is not too lengthy and IRES can be solved in reasonable time. The running time can be improved with tailored algorithms specifically designed for IRES, like the example FAST-IRES algorithm described in the previous sections.

Example Results—Computer Simulations

FIG. 7 through FIG. 9 show simulation results using the same lead field matrix for forward and inverse problem. The results presented in FIGS. 7 and 8 pertain to the case were the SNR of the simulated scalp potential is 20 dB and the same results are presented in FIG. 9 for the 10 dB case. As it can be seen in FIG. 7 IRES can distinguish between different source sizes and estimate the extent with good accuracy. In the left panel of FIG. 7, three different cases are presented with extents of 10, 20 and 30 mm, respectively. Comparing the simulated sources and estimation results shows that IRES can distinguish between different sources reasonably. The right panel in FIG. 7 shows the relation between the extent of the estimated and simulated source. The fitted line shows that IRES has small bias and minimal under/over-estimation on average. The variance of the estimated solutions is comparable to the estimated extent (about 50% of source extent). The overall trend is positive and indicates that IRES is relatively unbiased in estimating underlying source extent.

Figure 17:
FIG. 17 illustrates IRES sensitivity to source location and depth. Simulation results for four difficult cases are presented in this figure for two SNRs, i.e. 20 and 6 dB. The sources were simulated in the medial wall located in the interhemispheric region, medial temporal wall and sulci wall. The orientation of some of these deep sources is close to tangential direction.

Other measures such as LE, NOR and AUC are also important to assess the performance of IRES. In FIG. 8 the results of such different metrics can be seen. The localization error in sources with different extent is less than 5 mm over all. Note that the simulated sources were approximately categorized into three classes with average extent of 10, 20 and 30 mm, corresponding to the three colors seen in FIG. 7. This value is less for smaller sources and closer to 3 mm. Such a low localization error shows that IRES can localize the underlying extended sources with low bias. In a few cases (where the LE is greater than 12 mm) the simulated sources were split between the two hemispheres with an unconventional geometry, thus the solution was a bit widespread and not good. However some of the cases simulated in deeper regions like the medial temporal lobe or the medial wall of the inter-hemisphere have errors in the range of 5-10 mm. Results of some difficult simulation cases are provided in FIG. 17 and discussed further below. Additionally, to better understand the combined effect of LE and extent estimation, the normalized overlaps should be studied. Looking at FIG. 8 one can see that the overlap between the estimated and simulated source is relatively high and over 70% for smaller sources (on average) and close to 85% for larger sources. The fact that both NOR values are high show that not only the estimated and simulated sources overlap extensively with each other, but the estimation is neither an overestimation nor an underestimation of the spatial extent (in either case only one of the NOR values would be high and the other would be small). The high AUC values for various source sizes also indicate the overall high sensitivity and specificity of IRES as an estimator.

FIG. 9 shows the same results for the 10 dB case. Comparing FIG. 9 with FIG. 8 and FIG. 7, similar trends can be observed.

Figure 10:
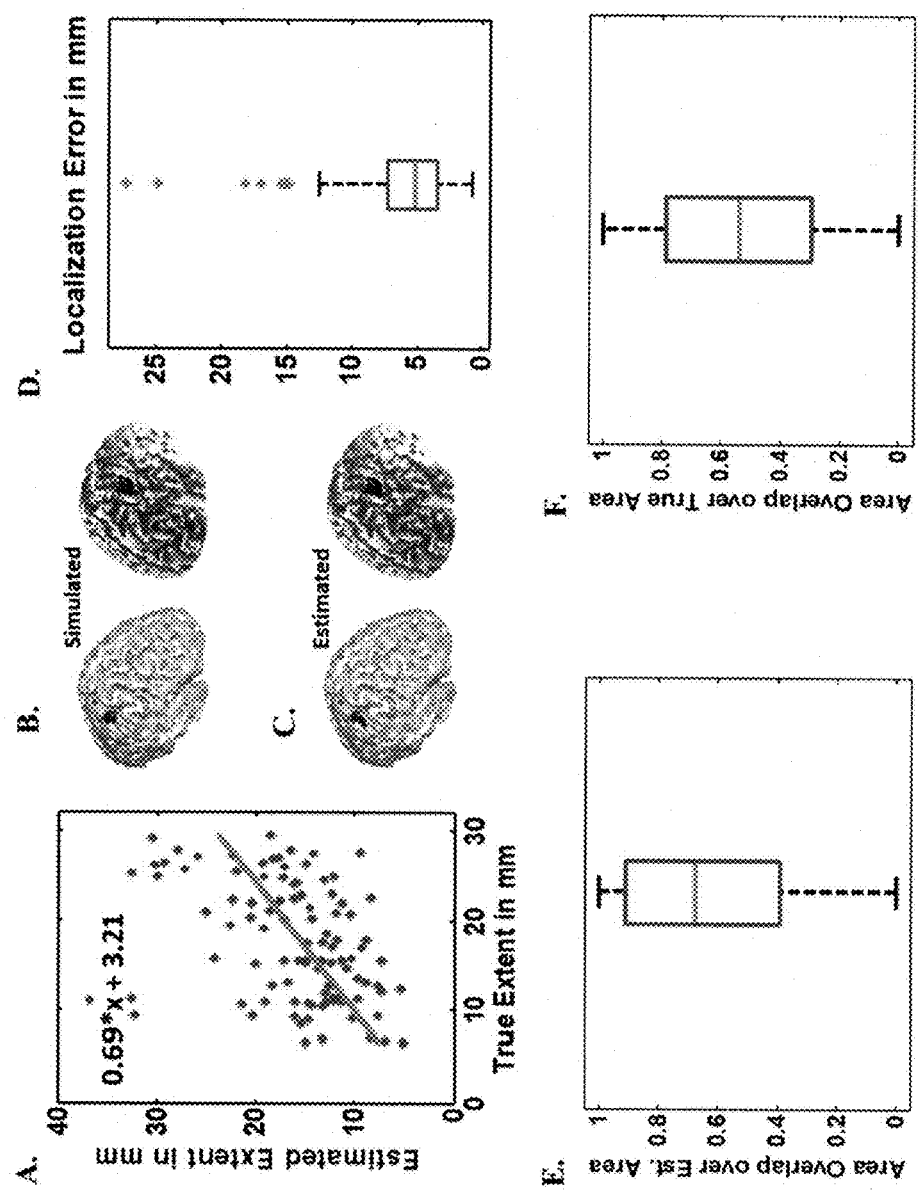
FIG. 10 provides Monte Carlo simulations of IRES imaging for the differing boundary element method (BEM) models with 6 dB SNR (in these models different electrical conductivity ratios, skull to brain conductivity ratio, was used to calculate the lead-field matrix used in the forward and inverse direction, in addition to a different grid for the forward and inverse problem, and also to observe the effect of such model variations on IRES performance). The estimated source extent is graphed against the true (simulated source) extent (A). Two examples of the target (true) sources (B) and their estimated sources (C) are provided. The localization error (D), normalized overlaps defined as overlap area over estimated source area (F) and overlap area over true source area (F), are presented to evaluate the performance of IRES (all data). The boxplots show the distribution of each metric to provide a brief statistical review of the distribution of these metrics for all of the data. The metrics and how to interpret them are further discussed below in relation to methods used.
Figure 11:
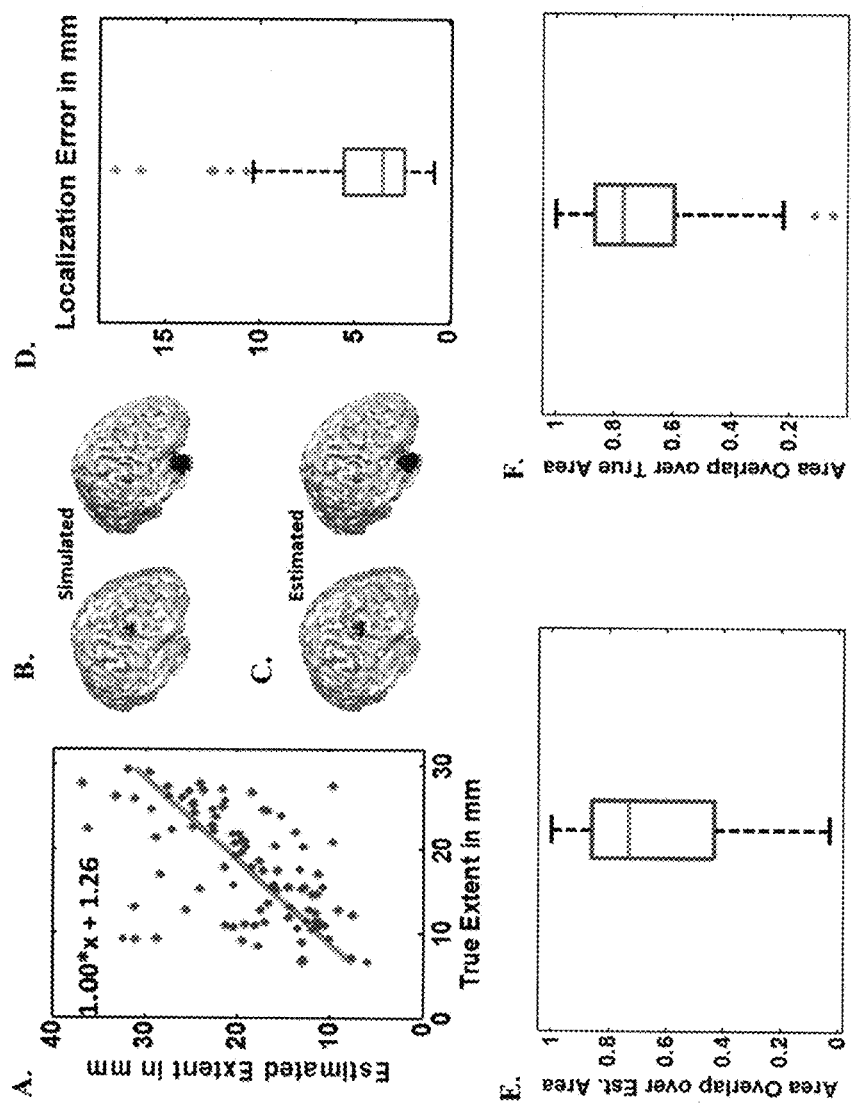
FIG. 11 provides Monte Carlo simulations of IRES imaging for the differing BEM models with 20 dB SNR. The estimated source extent is graphed against the true (simulated source) extent (A). Two examples of the target (true) sources (B) and their estimated sources (C) are provided. The localization error (D), normalized overlaps defined as overlap area over estimated source area (F) and overlap area over true source area (F), are presented to evaluate the performance of IRES (all data). The boxplots show the distribution of each metric to provide a brief statistical review of the distribution of these metrics for all of the data. The metrics and how to interpret them are further discussed below in relation to methods used.

FIG. 10 and FIG. 11 show simulation results when different forward and inverse models (in terms of grid size and conductivity) are used for two cases of 6 dB and 20 dB SNR. The results in FIG. 10 show an underestimation for the extent. The localization error is as low as 5 mm and the NOR is ~60%-70% on average. Comparing the same results when SNR is set to 20 dB, much better results can be obtained. Referring to FIG. 11 it can be seen that the extent estimation is with minimal bias with localization error of 3 mm (on average) and high NOR metrics (80% for both values on average). The slight decline in IRES performance in noisier conditions (FIG. 9 and FIG. 10) is expected due to increased levels of noise interference.

Figure 14:
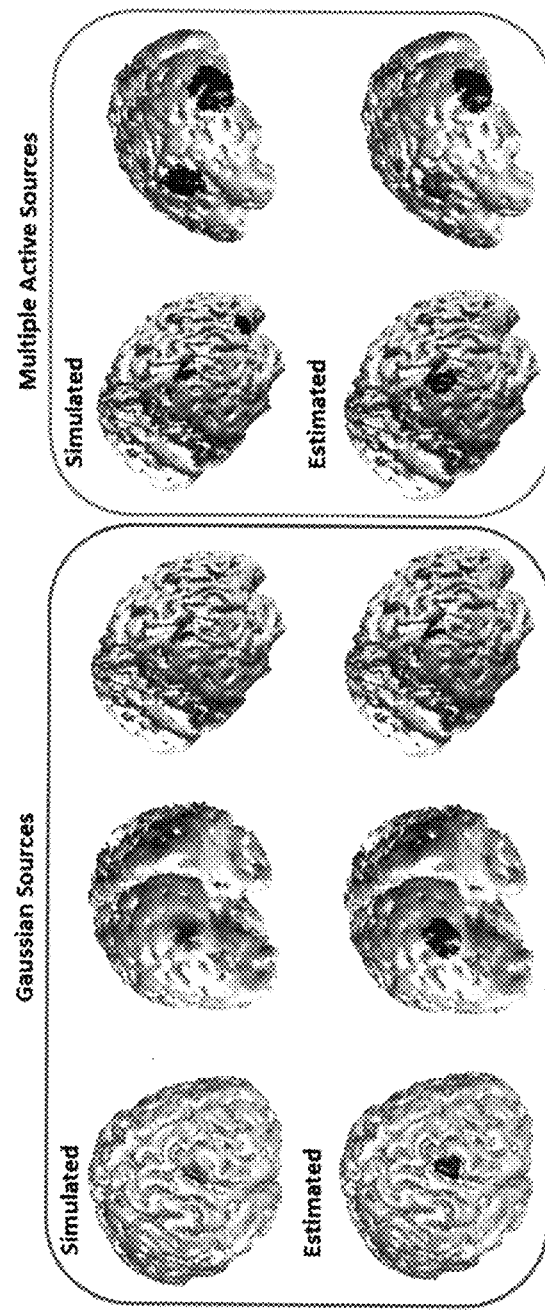
FIG. 14 provides model violation scenarios. Examples of IRES performance when Gaussian sources (left panels) and multiple active sources (right panel) are simulated as underlying sources for a 6 dB SNR. Simulated (true) sources are depicted in the top row and estimated sources on the bottom row.

A few examples when source amplitude is not constant and also when multiple sources are simultaneously active, are presented in FIG. 14. The variation of source amplitude was governed by a normal distribution, meaning that the amplitude of the dipoles decreased exponentially as the distance of the dipoles increased from the center of the source distribution (patch).

These simulation results show that IRES is robust against noise and changes in model parameters such as grid size and conductivity. IRES can perform well when multiple sources are active or when source amplitude varies within the source extent.

Example Results—Clinical Data Analysis

Figure 18:
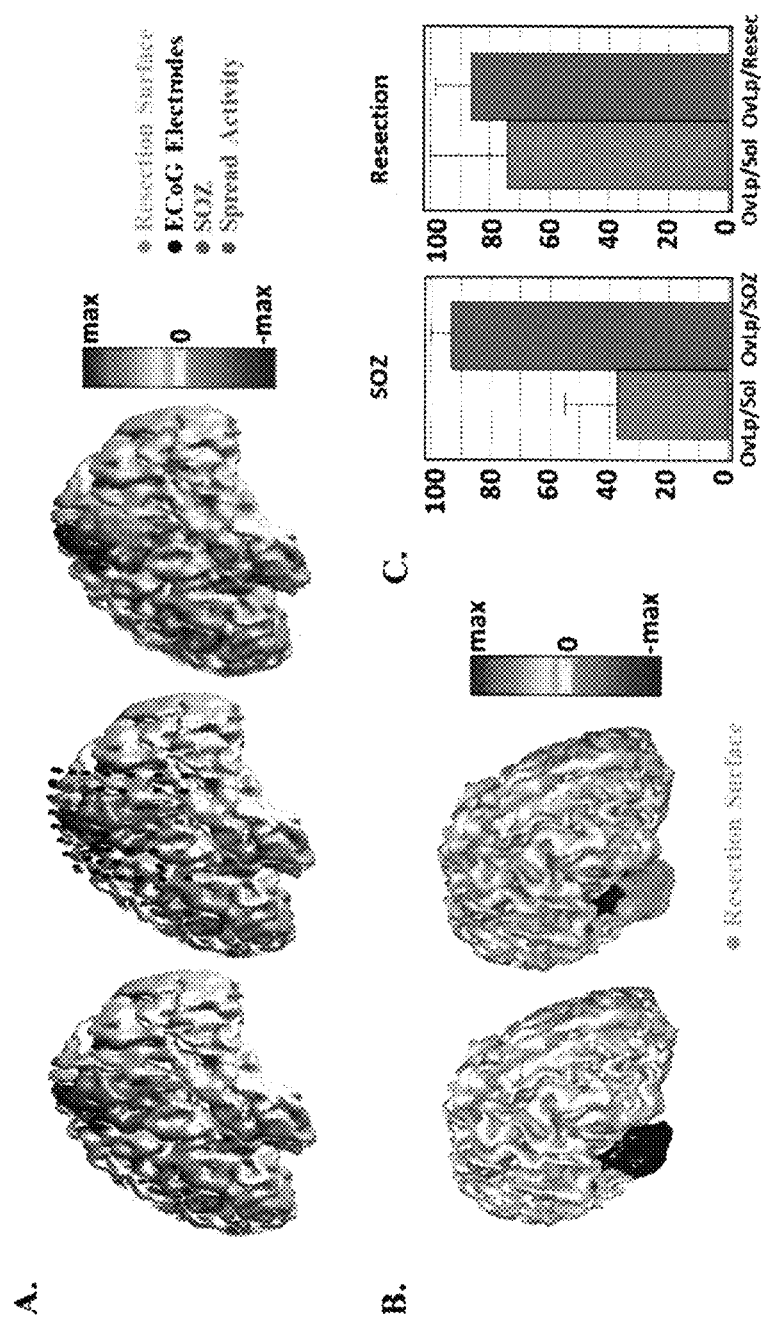
FIG. 18 provides source extent estimation results in all patients. (A) Estimated results by IRES in a parietal epilepsy patient compared with SOZ determined from the intracranial recordings (middle) and surgical resection (right). (B) Estimation results of source extent computed by VIRES in another temporal lobe epilepsy patient compared with surgical resection. (C) Summary of quantitative results of the source extent estimation by calculating the area overlapping of the estimated source with SOZ and resection. The overlap area is normalized by either the solution area or resection/SOZ area.

The patient data analysis is summarized in FIGS. 15 and 18. FIG. 15 shows the results of a temporal lobe epilepsy patient who underwent invasive EEG recording and ultimately surgical resection. In this case different timing was tested to examine the effect of estimation results at different time instances around the peak. It can be seen in panel A of FIG. 15, that five different timings (instances) were tested, two prior to peak time, the peak time and two after the peak corresponding to 50% and 70% rising phase, peak and 70% and 50% falling time. Looking at the estimated solution at different timings, it is clear that the solution is stable within tens of milliseconds around the peak and the epileptic activity does not propagate too much. This might be due to the fact that the averaged inter-ictal spikes arise from the irritative zone which is larger than the SOZ, so the propagation of activity might not even be observable using the average spike. Comparing the results of IRES with the resection in panel B in FIG. 15 it can be seen that the estimated solution coincides within the resection very well. Looking at the SOZ electrodes colored pink (1515) in panel B in FIG. 15 it is also observed that the SOZ electrodes are covered by the solution. SOZ region is very focal so it is challenging to obtain a solution which can be in full concordance with it and as it can be seen, sometimes the SOZ region is not continuous (electrodes are not always right next to each other); nonetheless the estimated solution by IRES is in concordance with the clinical findings.

In order to further test the proposed IRES approach two more patients were studied; one temporal case with anterior tip of temporal lobe resection (and thus a smaller resection area) and an extra-temporal case (fronto-parietal). Referring to panel A (top) in FIG. 18 it can be seen that the estimated solution includes most of the SOZ electrodes and coincides well with the resection. This implies that IRES does well for extra-temporal lobe cases as well as temporal cases. Given the fact that not all the SOZ electrodes are close to the resection, the estimated solution is a bit spread towards those SOZ electrodes and the neighboring regions thus extending beyond the resected region. In panel B (bottom left) in FIG. 18 the results of the second temporal case can be found. This patient did not have any intra-cranial EEG recordings. Panel C (bottom right) of FIG. 18 reports the quantitative analyses for these three patients. In order to assess how well the estimated results match the clinical findings, the overlap between the solution and the resection and the SOZ was calculated. Then this overlap area was either divided by the solution area or the resection/SOZ area. The results are classified as resection and SOZ indicating the clinical finding, i.e. SOZ or resection, used to assess the estimated solutions.

Looking at panel C in FIG. 18 it can be seen that the IRES solution generally covers the SOZ very well but also extends beyond the SOZ giving an overestimated solution. Looking at the right bar-plot it can be seen that this is not the case when comparing the IRES solution to resected area.

Note that for temporal lobe epilepsy cases, due to more geometrical complexity of the cortex in the temporal region (compared to other locations within the brain) and the fact that mesio-temporal region is not directly recorded by the electrodes over the temporal region, Vector-based IRES (VIRES) was used instead of IRES (mathematical details of VIRES are given in Appendix B below). VIRES basically relaxes the orientation constraint of the dipoles (being orthogonal to the cortical surface as implemented by IRES) and leaves that as a variable to be estimated.

Example Results—Testing Embodiments of IRES on Public Data Sets

To further evaluate IRES, the algorithm was tested on the Brainstorm epilepsy data which is publicly available at http://neuroimage.usc.edu/brainstorm. The tutorial at http://neuroimage.usc.edu/brainstorm/Tutorials/Epilepsy includes the anonymous data of a patient suffering from focal fronto-parietal epilepsy, who underwent surgery and is seizure-free within a 5 year follow-up duration. The patient underwent intracranial EEG (iEEG) recording prior to surgery. The iEEG study results as well as the post-operational MRI are not available in the data set but are presented in a published paper elsewhere. The procedure outlined in the Brainstorm tutorial was followed to get the average spikes and the head model, with the exception of the head model conductivity (ratio) for which we used the conductivities we have used so far, throughout the paper.

Figure 20:
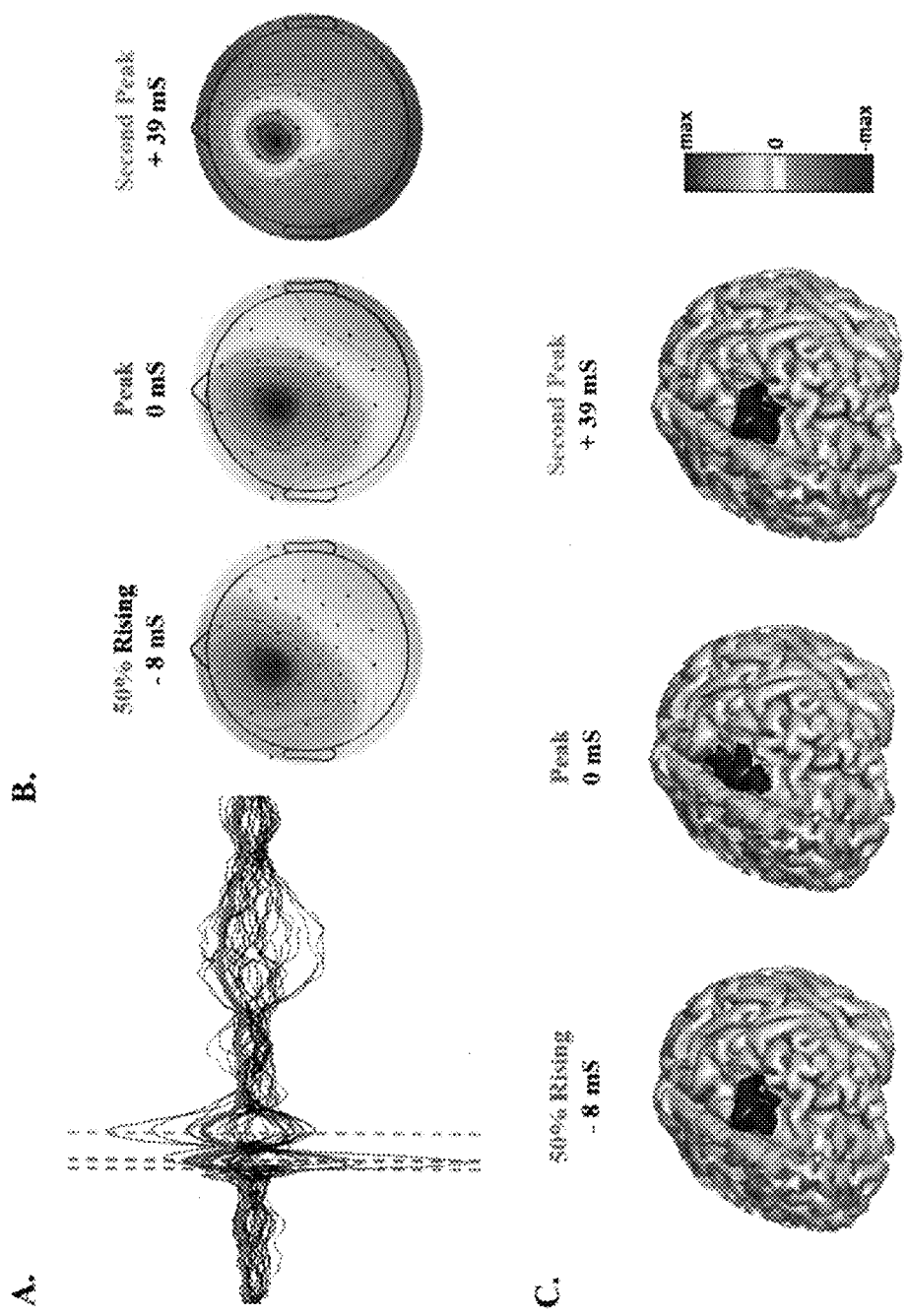
FIG. 20 illustrates testing IRES on the brainstorm epilepsy tutorial data. (A) Scalp EEG waveforms of the inter-ictal spike in butterfly plot on top of the mean global field power (in red). (B) Scalp potential maps of the half rising, first peak and the second peak. (C) IRES results at the specified time-points in the inter-ictal spike.

FIG. 20 shows the IRES solutions in this data set. Comparing these results with the clinical findings reported in the literature, the obtained results are in well accordance with such findings.

Computer simulations were conducted to assess the effect of thresholding on IRES in comparison to FVR. For the given target source (simulated source) it can be seen that thresholding has little effect on IRES while it affects the estimated extent by FVR (FIG. 1). Thresholding is usually applied to the estimated source imaging solution when there is no objective means to determine the source extent. In order to separate the background activity from pertinent brain activity (such as epileptogenic are in the brain), a threshold needs to be applied when using other algorithms. It is observed that sometimes, a subjective threshold of 50%-70% is applied to the solution; that is, the amplitude of source locations smaller than 50%-70% of the maximum amplitude are set to zero. As FIG. 1 depicts, thresholding will affect the extent of the estimated source. This illustrates the difficulty of subjective thresholding and the importance of being able to objectively determine the threshold (which IRES is capable of).

Figure 12:
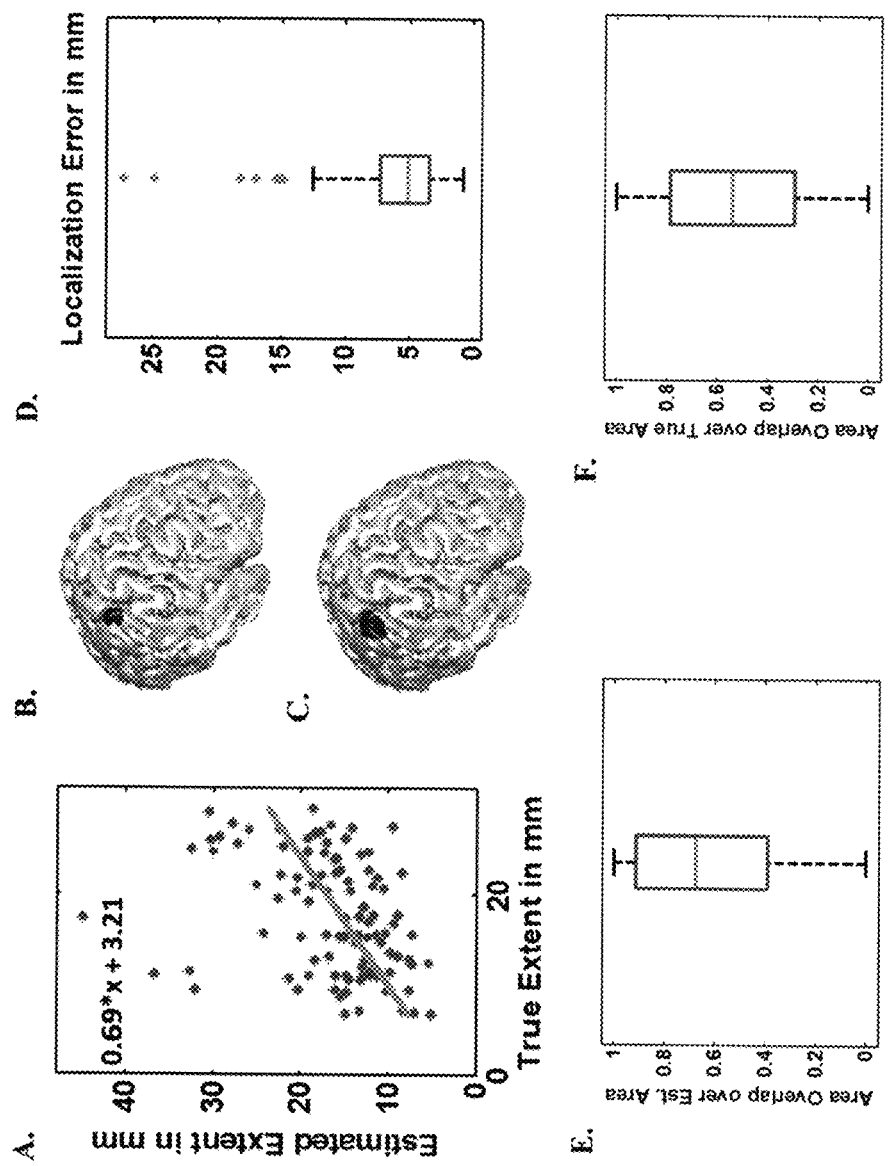
FIG. 12 provides Monte Carlo simulations of IRES imaging for the concurring BEM Models with different grid meshes at 6 dB SNR. The estimated source extent is graphed against the true (simulated source) extent (A). An example of the target (true) source (B) and its estimated source (C). The localization error (D), normalized overlaps defined as overlap area over estimated source area (F) and overlap area over true source area (F), are presented to evaluate the performance of IRES (all data). The boxplots show the distribution of each metric to provide a brief statistical review of the distribution of these metrics for all of the data. The metrics and how to interpret them are further discussed below in relation to methods used.
Figure 13:
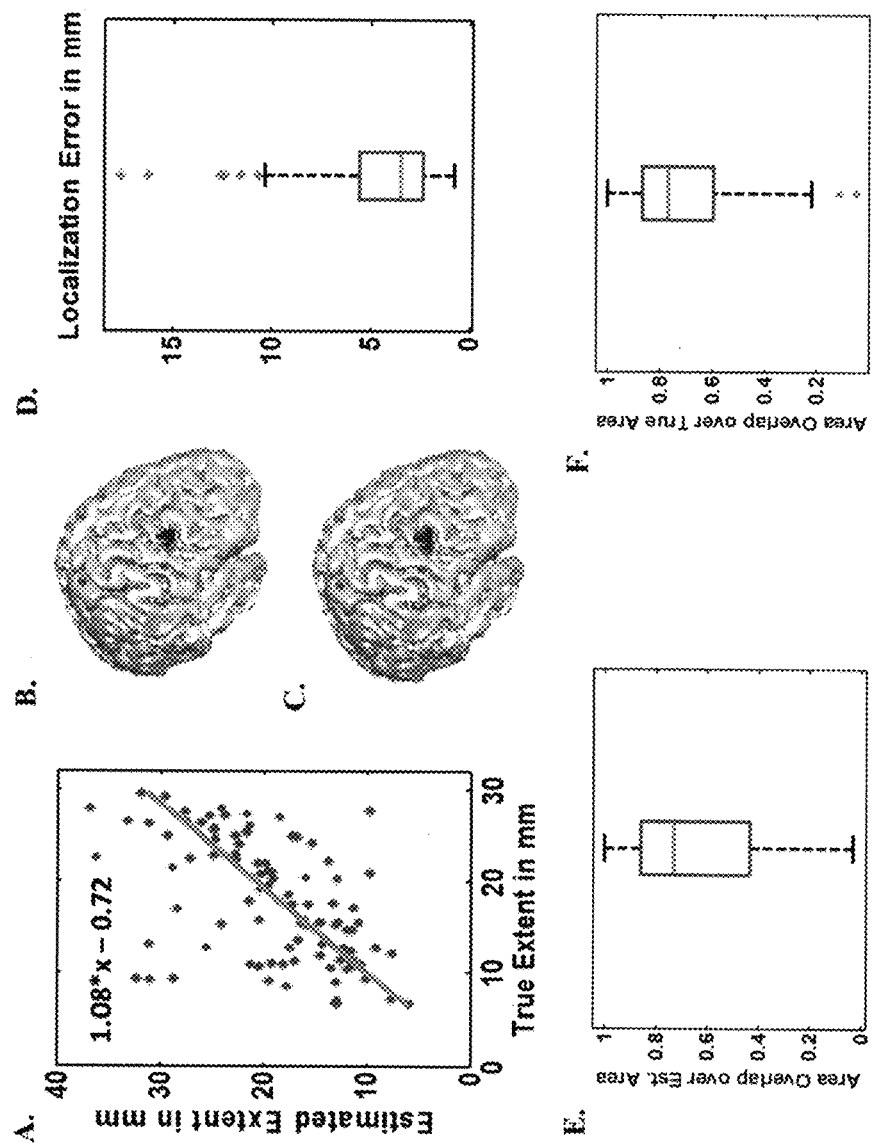
FIG. 13 provides Monte Carlo simulations of IRES imaging for the concurring BEM Models with different grid meshes at 20 dB SNR. The estimated source extent is graphed against the true (simulated source) extent (A). An example of the target (true) source (B) and its estimated source (C). The localization error (D), normalized overlaps defined as overlap area over estimated source area (E) and overlap area over true source area (F), are presented to evaluate the performance of IRES (all data). The boxplots show the distribution of each metric to provide a brief statistical review of the distribution of these metrics for all of the data. The metrics and how to interpret them are further discussed below in relation to methods used.

The simulation results when the conductivity values of the inverse BEM model concurred with the forward BEM models (while different grid meshes were used for forward and inverse) are presented in FIG. 12 and FIG. 13, for 6 dB and 20 dB SNRs, respectively; these should not to be confused with results depicted in FIG. 10 and FIG. 11 which pertain to the case where the conductivities of the forward and inverse BEM models were also different, in addition to different meshing for forward and inverse models, as outlined in the Methods section above. Referring to FIGS. 12 and 13 it is perceivable that while the estimated extent is not as accurate as in the case of 20 dB, IRES returns good results. The localization error is on average about 5 mm and the overlap between the estimated solution and simulated (target) sources are high (for both measures) reaching close to 70% overlap (FIG. 12). The average localization error of 3 mm and high overlap between estimation and target (about 80% for both measures) indicates the strong performance even with different forward models (grid meshes) (FIG. 13). Another interesting observation is that not a huge difference can be seen between the two models (where different skull-brain conductivity ratio is used) by comparing FIG. 12 and FIG. 13 to FIG. 10 and FIG. 11.

To further evaluate and compare the performance of IRES with other methods, the same simulations (6 dB SNR) were conducted but the inverse algorithms used were cLORETA and FVR. The results can be seen in FIG. 21 and FIG. 22 for cLOREAT and FVR, respectively. Looking at the extent estimation curves (panel A in each figure) it is difficult to find a clear relation between the estimated and target sources. It is worthy of attention that while localization error was reasonable in these methods (FVR doing better than cLORETA) the overlaps were not satisfactory for both methods. Either there was an asymmetry between the overlap measures (one high and the other low) which indicates over/under-estimated solutions (in terms of source extent), or low overlaps for both measures.

Figure 23:
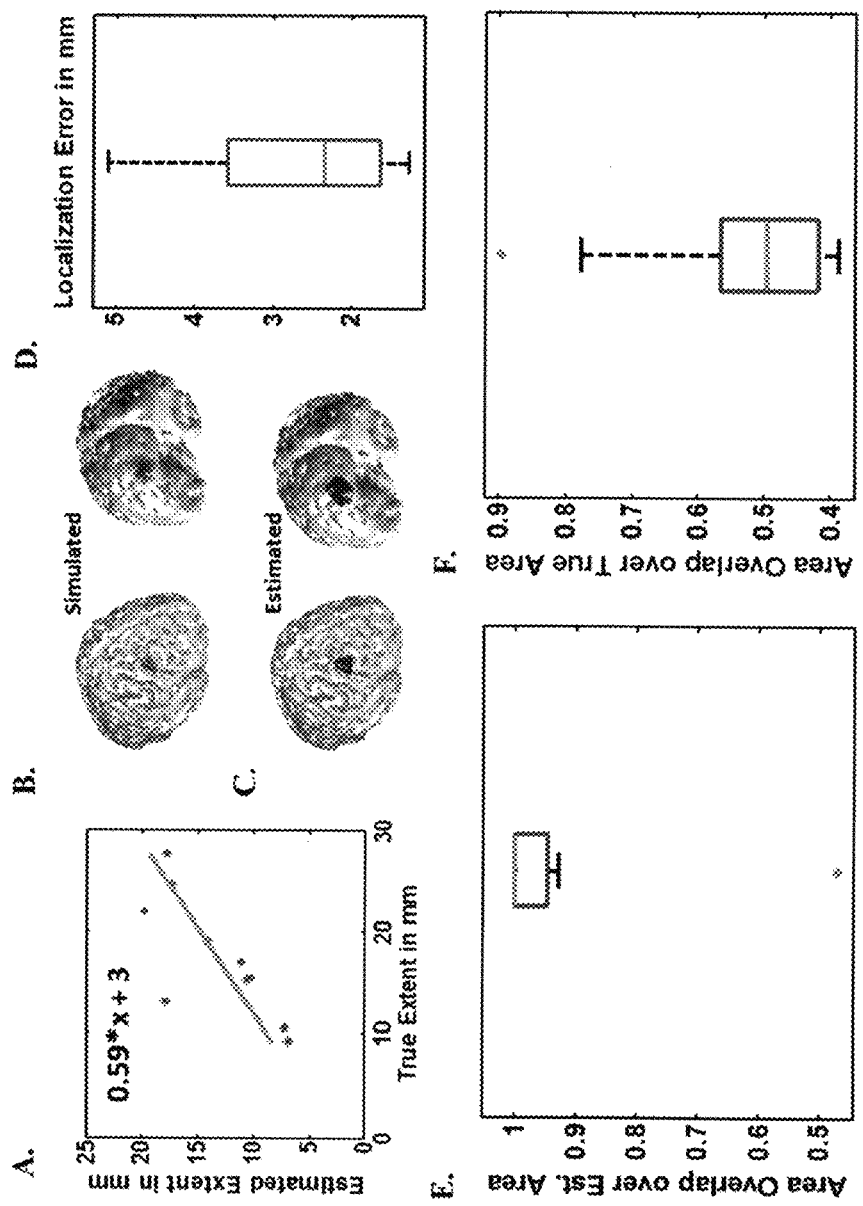
FIG. 23 provides Monte Carlo simulations for Gaussian sources (large variations) at 10 dB SNR (IRES). The estimated source extent is graphed against the true (simulated source) extent (A). Two examples of the target (true) sources (B) and their estimated sources using the IRES algorithm (C) are provided. The localization Error (D), Normalized overlaps defined as overlap area over estimated source area (E) and overlap area over true source area (F), are presented to evaluate the performance of IRES (all data). The boxplots show the distribution of each metric to provide a brief statistical review of the distribution of these metrics for all of the data. The metrics and how to interpret them are further discussed below in relation to methods used.
Figure 24:
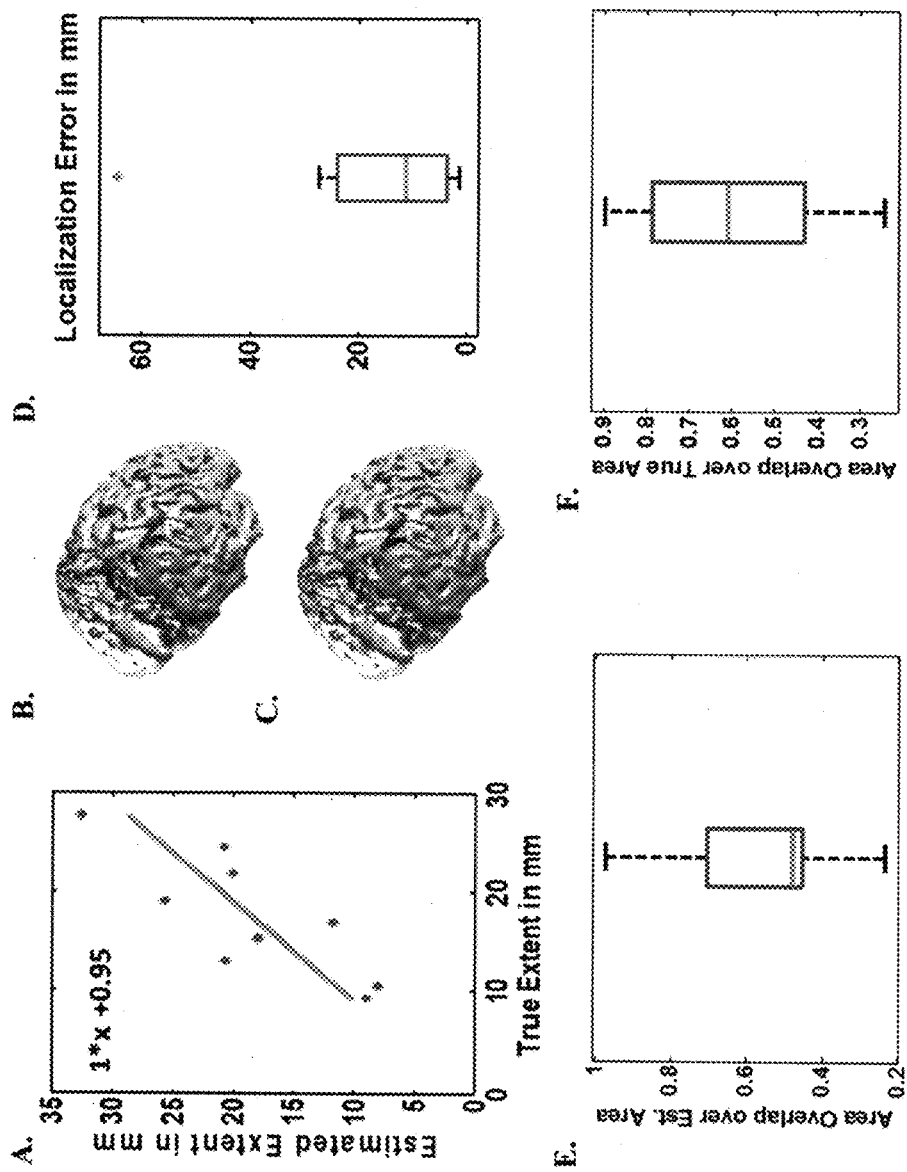
FIG. 24 provides Monte Carlo simulations for Gaussian sources (small variations) at 10 dB SNR (IRES). The estimated source extent is graphed against the true (simulated source) extent (A). An example of the target (true) source (B) and its estimated source using the IRES algorithm (C). The localization Error (D), Normalized overlaps defined as overlap area over estimated source area (E) and overlap area over true source area (F), are presented to evaluate the performance of IRES (all data). The boxplots show the distribution of each metric to provide a brief statistical review of the distribution of these metrics for all of the data. The metrics and how to interpret them are further discussed below in relation to methods used.
Figure 25:
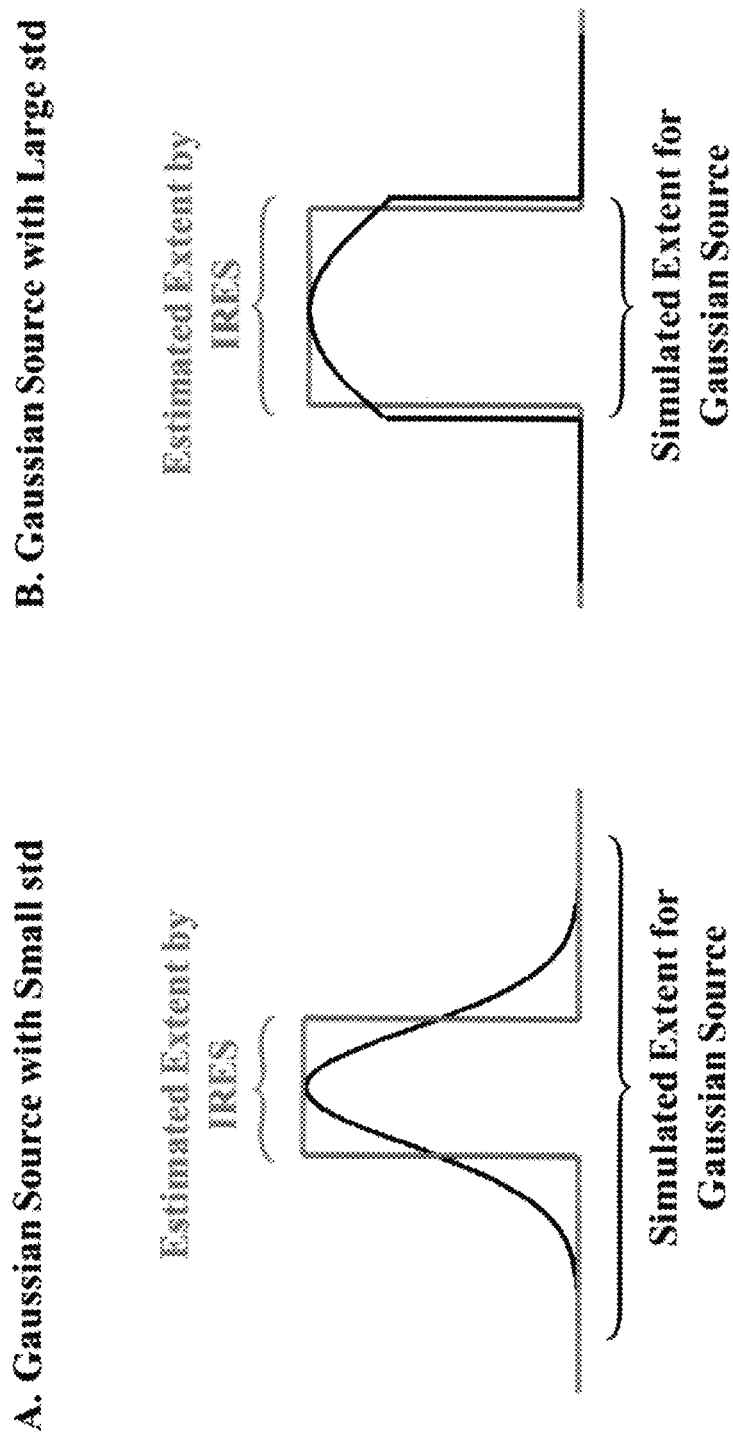
FIG. 25 provides a schematic explanation of IRES estimation for underlying sources with varying amplitude over the source extent. IRES can confuse smaller amplitudes with noisy background and underestimate the source extent by excluding those sources. Variations that do not fall into noise range can still be detected. IRES tends to prefer flat solutions.
Figure 26:
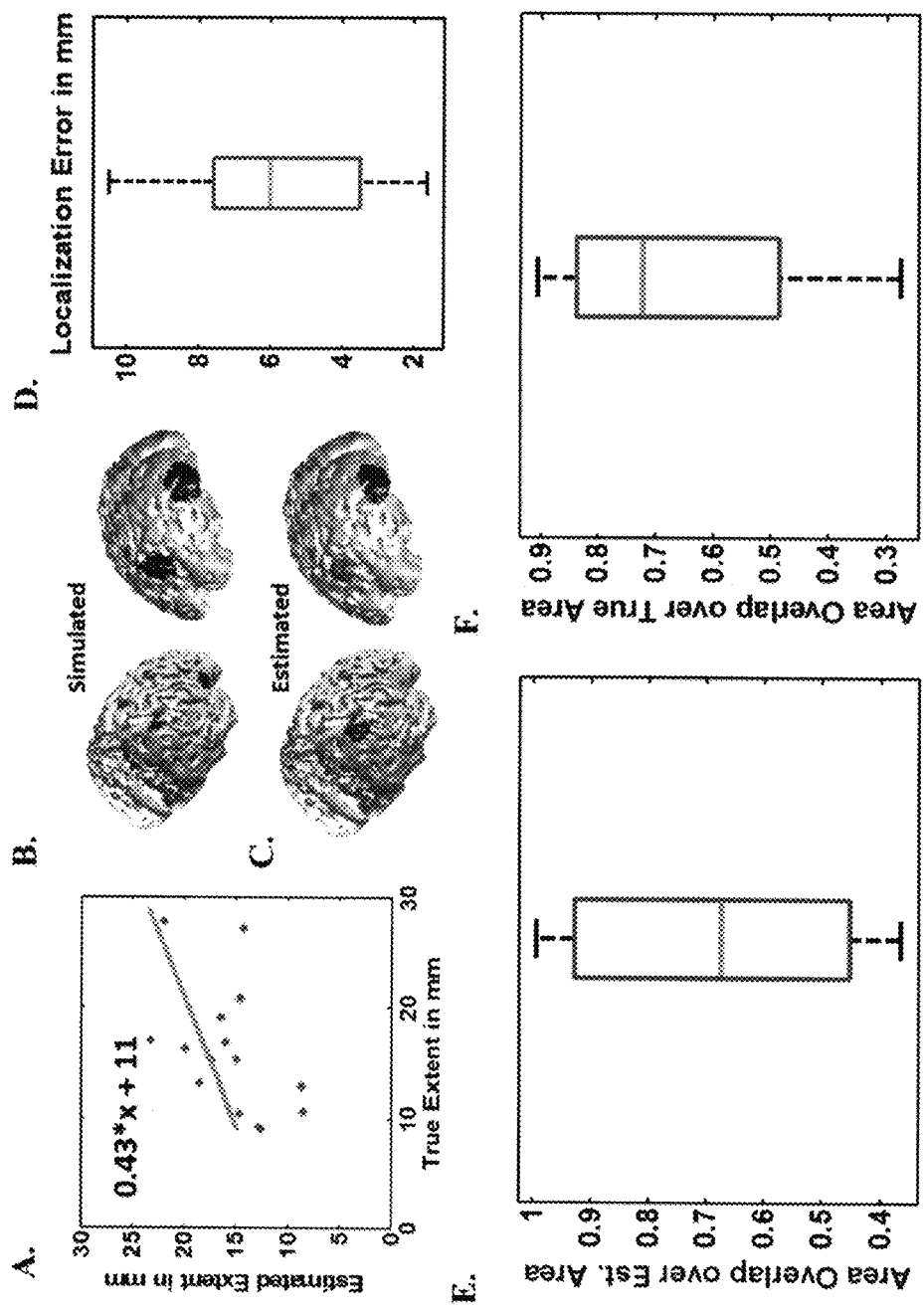
FIG. 26 provides Monte Carlo simulations for two active sources at 10 dB SNR (IRES). The estimated source extent is graphed against the true (simulated source) extent (A). Two examples of the target (true) sources (B) and their estimated sources using IRES algorithm (C) are provided. The localization Error (D), Normalized overlaps defined as overlap area over estimated source area (E) and overlap area over true source area (F), are presented to evaluate the performance of IRES (all data). The boxplots show the distribution of each metric to provide a brief statistical review of the distribution of these metrics for all of the data. The metrics and how to interpret them are further discussed below in relation to methods used.

To further investigate IRES capabilities another test was performed. Instead of having constant sources, the value of the source was varied along the source extent. A Gaussian model was used to pursue this line of investigation. The amplitude of the source falls of following a normal distribution, proportional to dipoles' distance to the center of patch. To test different cases the standard deviation of the normal distribution or the rate of change was tested for two different scenarios. One for the case where the standard deviation (STD) was set equal to half the extent size (as extent size varies from source to source) where more variations would be seen and another case where the STD was set equal to the extent size to obtain mild variations. Note that the STD was defined based on extent size, to create a more similar condition for sources with different size (fixing STD to a constant would have had different effects on sources with different extent sizes and is thus avoided in this scheme). The results and examples of this simulation can be seen in FIG. 23 and FIG. 24. In FIG. 23 where source variations are more rapid, it is clear that the algorithm underestimates the extent size compared to the situation depicted in FIG. 24. It seems that IRES disregards the tails of the distribution where the signal amplitude is low and probably confuses those values with noise. This confusion could potentially be overcome in higher SNR values (the SNR value was set to 10 dB and 20 different scenarios were tested in the "Gaussian Simulation" case). For instance, in FIG. 24, which pertains to slowly varying sources, it can be observed that a better estimation of the extent is given. This idea is schematically depicted in FIG. 25. Given the reasonable localization errors and overlaps, it can be seen that IRES can handle such variations relatively well, although it may enforce uniformity in amplitude of the estimated source in certain implementations.

Another attempt to test IRES was posed by simulating two active sources at the same time in various locations to assess IRES performance. Like the previous simulations ("Gaussian Simulations") we tested 20 different scenarios in a 10 dB SNR. The results can be seen in FIG. 26. The localization error is low (~6 mm) and the overlaps are pretty high. Referring to panel A in FIG. 26 it can be seen that a lot of points are following the identity line while a few deviating violators. In any case it can be seen that IRES can handle different scenarios pretty well and shows robustness against noise and modelling parameters (mesh size and conductivity).

Figure 16:
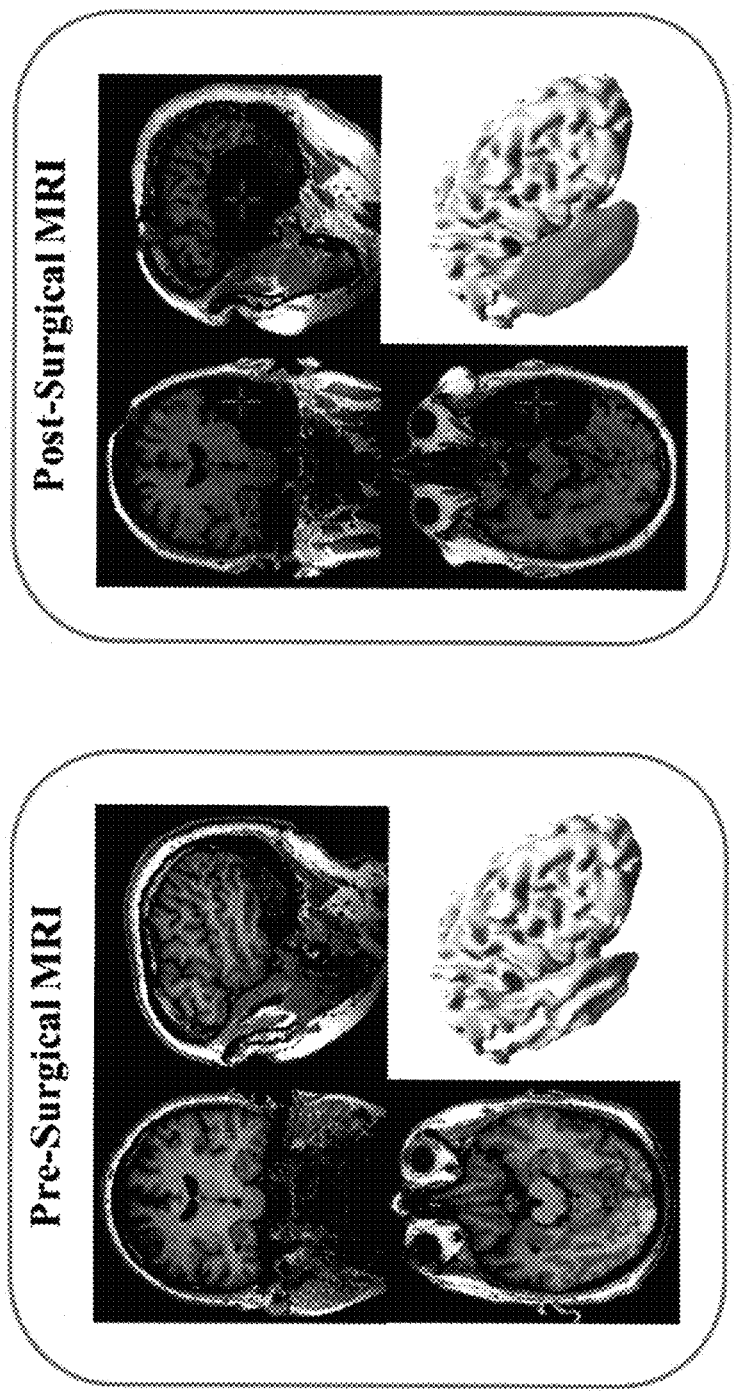
FIG. 16 provides a pre-surgical and post-surgical MRI of a patient with temporal lobe epilepsy. The resected volume can be seen in the post images very clearly.

Some MRI images prior to and after surgery are also shown in FIG. 16, to better visualize the resection volume.

Figure 19:
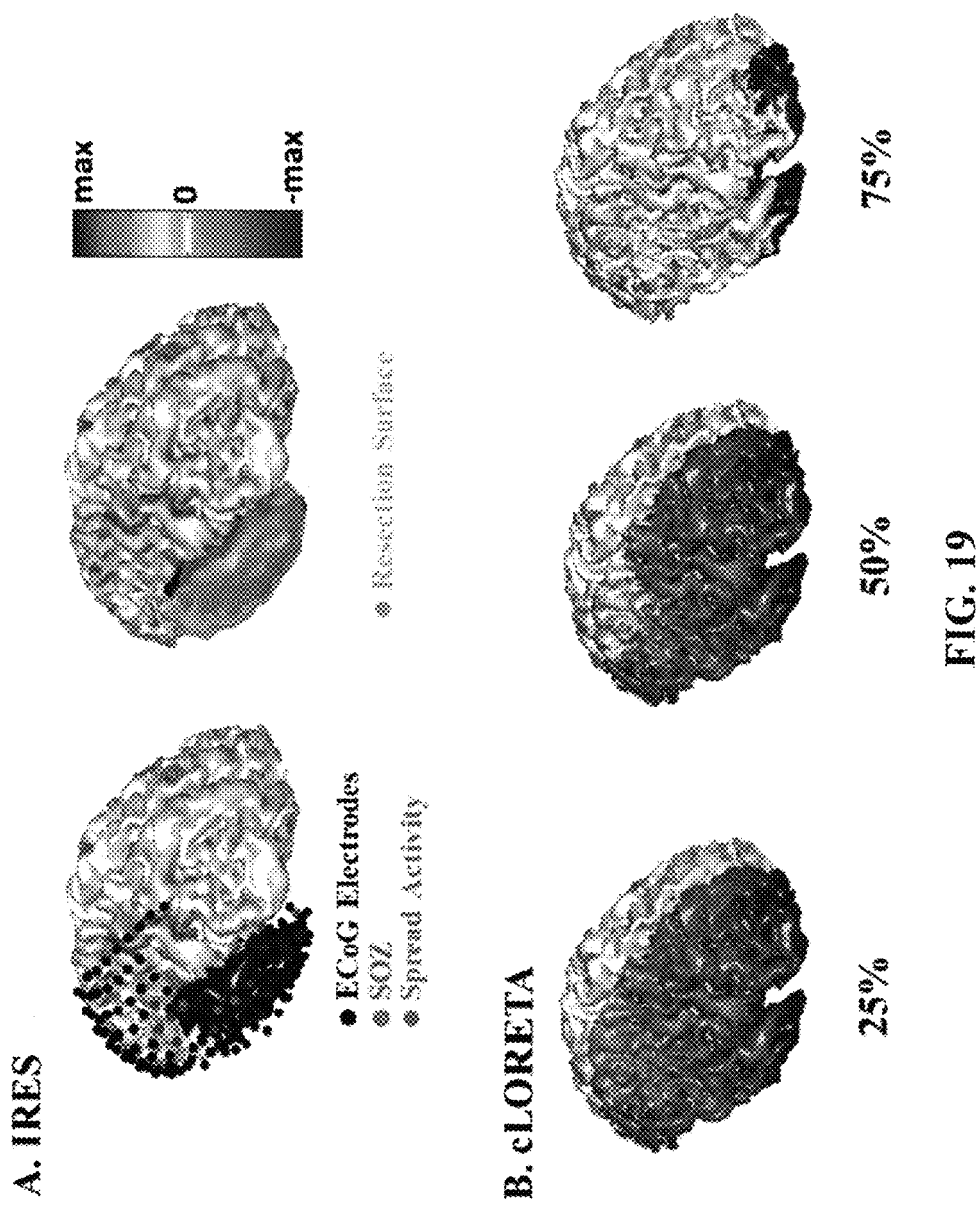
FIG. 19 illustrates cLORETA reconstruction in a patient with temporal lobe epilepsy. The IRES solution is compared to clinical findings (A) such as resection volume and SOZ iEEG electrodes. The inverse problem was also solved using cLORETA and different threshold values were applied to this solution (B), to better visualize the effect of thresholding on the solution extent.

We also solved the inverse problem using cLORETA in case of a patient with temporal lobe epilepsy. The results are depicted in FIG. 19. It can be seen that firstly, the effect of thresholding is very evident on determining the extent and that (at least in this case) the chosen method did not cover the SOZ electrodes in the superior temporal region.

As discussed, this disclosure provides a new inverse approach referred to as iterative reweighted edge sparsity (IRES). As the simulation results suggest, this approach is capable of distinguishing between sources with different sizes. The simulation results suggest that IRES not only localizes the underlying source but can also provide an estimate of the extent of the underlying source, as well. Importantly, IRES produces extended sources without the need for any kind of subjectively-determined thresholding. The initial clinical evaluation study in focal epilepsy patients also shows good concordance between clinical findings (such as resection and SOZ) with IRES solution. This evinces the practicality of IRES in clinical applications such as pre-surgical planning for pharmacoresistant focal epilepsy. Although we tested the IRES in imaging focal epilepsy sources, IRES is not limited to epilepsy source localization, but is applicable to imaging brain sources in other disorders or in healthy subjects from noninvasive EEG (or MEG), as well as other non-brain applications.

Figure 27:
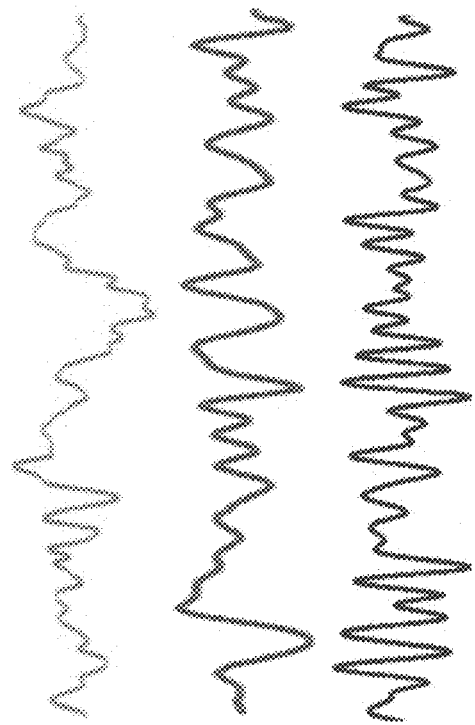
FIG. 27 provides an illustration of estimating time course of source activity. in accordance with one or more embodiments. The left panel shows three areas of electrical activity in a brain, and the right panel shows the time course of these estimated sources over time.
Figure 27:

In other example applications of IRES is to estimate time-courses of electrical activity. When a source distribution is estimated from EEG (or MEG), the time evolution of the estimated source signals at a given location can be extracted and displayed to reflect the temporal dynamics at the brain location. Such time courses can be used to perform further network analysis. FIG. 27 shows an example of time courses of source activity estimated from EEG using IRES technique.

Examples of other applications include: source imaging of other brain activity and non-brain activity. Brain applications include mapping the eloquent cortex to assist in neurosurgery where the precise determination of cortical extents is critical, mapping brain sensory network, motor network, visual network, cognitive networks, or even brain networks involving in pain processing, as well as brain mapping of other neurological and psychiatric disorders. Non-brain applications include imaging of cardiac and muscular activities. Cardiac arrhythmia is one of the major causes of public health burden. Cardiac arrhythmias are commonly ablated using radio-frequency energy or other means of ablation. Accurate localization of arrhythmogenetic origins and areas is important for effective treatment of cardiac arrhythmia. IRES can be applied to mapping cardiac electrical activity and the originating areas responsible for cardiac arrhythmia from recorded ECG or MCG, or even from catheter electrical recordings. The principles and algorithms disclosed above can be applicable to such ECG/MCG with the aid of torso volume conductor model to determine the cardiac electrical activity of arrhythmia, including but not limited to atrial fibrillation, atrial flutters, premature ventricular contractions, ventricular tachycardia. IRES can be applied to any underlying dynamic networks and the aforementioned applications are just a few examples.

Merits and Novelty of Embodiments of IRES and Parameter Selection

Prior algorithms have been able to produce relatively focal solutions, but they do not provide solutions with clear edges between background and desired activity and thus determining how to discard the tails of the solution distribution, i.e. thresholding, is difficult. IRES, on the other hand, can achieve this by imposing sparsity on the spatial gradient which in turn creates visible edges. It is noted that certain prior algorithms do not intend to find the extent of the underlying sources like IRES and instead aim to model other physiologically plausible characteristics.

There are algorithms formulated and operating within the Bayesian framework, such as maximum entropy on the mean (MEM)-type algorithms, and they can be combined with cortex parcelization. These algorithms use Otsu's thresholding method to separate the background noise from active sources objectively. However, there is an implicit assumption in Otsu's method that classes (say, background and desired signal) are distinguished enough, to be separated well with a threshold. This, however, depends on the inverse method used. Conventional methods do not provide strong discriminants, and the threshold might not be "unique" in practice. In example implementations of IRES, no parcelization is used. Additionally, example embodiments of IRES do not work within the Bayesian framework and are formulated as a series of convex optimization problems. Bayesian methods usually have complex formulations and are more computationally demanding (i.e., take relatively longer to run).

IRES, in certain embodiments, operates within a TV-L1 framework. This means that the sparsity is enforced on the edges as well as the solution itself. Within this framework data driven iterative reweighting are applied to IRES estimates at each step to get rid of small amplitude dipoles to obtain more accurate estimates. The formulation of IRES is simple yet effective and as tested by our extensive simulations, provides useful information about the source extent.

Another feature of example embodiments of IRES is its iterative reweighting technique. This procedure enables IRES to improve estimation by disregarding the locations that are more probable to lie outside the extent of the underlying source. Since the amplitude of the dipoles corresponding to locations outside the underlying source is smaller than dipoles closer to or within the underlying source (this is due to the formulation of the problem where spatially focused sources with zero background are preferred) it is reasonable to focus less on locations for which the associated dipoles have very low amplitudes. Additionally, after a few iterations, IRES converges to a solution which is zero in the background, i.e. a focused solution is obtained, so an extended solution is reached without applying any threshold. Due to the limited number of iterations and mostly due to the way existing convex optimization problems solvers work a perfect zero background might not be obtained but the amplitude of dipoles located in the background is typically less than 3% of dipoles with maximum amplitude.

The two features of IRES, namely the iteration and use of sparse signal processing techniques, makes IRES unique and can also explain the good performance of IRES in providing extended solutions which estimate the extent of the underlying source well. The parameters of the SOCP optimization problem in (3) should be selected carefully, to enhance how well IRES works. As discussed previously the L-Curve approach may be adopted to determine $\alpha$. The L-Curve in general is a tool to examine the dependency of level sets of the optimization problem to a certain parameter of the problem when the constraints are fixed. In our problem when $\beta$ is determined ($\beta$ intuitively determines noise level and is calculated based on the discrepancy principle) the constraint is fixed and then for different values of $\alpha$ the optimization problem is solved to find the optimum solution of the optimization problem for the given $\alpha$. For the obtained solution j* the pair ($\|j\|_1$* and $\|Vj\|_1$*) are graphed in a plot like FIG. 3 ($\|j\|_1$ and $\|Vj\|_1$ are the two terms of the goal function in (2)). The curve obtained for different values of $\alpha$ (level set of the goal function) which are the best pair of ($\|j\|_1$, $\|Vj\|_1$) that can be achieved given a fixed constraint and a fixed $\alpha$ value, can show the dependency of the two terms on parameter $\alpha$. If the curve has a clear pointed bending (knee), selecting the value of $\alpha$ around the knee is equal to selecting the Pareto-optimal pair (this means that for any other value of $\alpha$ that is selected, either $\|j\|_1$ or $\|Vj\|_1$ will be larger than the values of $\|j\|_1$ or $\|Vj\|_1$ of the knee). In this manner the (Pareto) optimal value of $\alpha$ can be selected. Another way to think about this is to imagine that for a fixed budget ($\beta$) the dependence curve of costs ($\|j\|_1$ and $\|Vj\|_1$) are obtained (also called "utility curve" in other fields such as microeconomics). The best way to minimize costs is to find the cost pair ($\|j\|_1$* and $\|Vj\|_1$*) for which all other pairs are (Pareto) greater, meaning that either one will be larger (compared to $\|j\|_1$* and $\|Vj\|_1$*). In the framework of Pareto-optimality the L-Curve formed from the level sets of the optimization problem, can determine the optimal value of $\alpha$. The hyper-parameter $\beta$ can be determined using the discrepancy principle. $\beta$ ultimately determines the probability of capturing noise. Another way to look at this is to note that $\beta$ determines how large the constraint space will be. In other words, selecting a larger $\beta$ corresponds to searching for an optimal solution within a larger solution space; this translates into relaxing the parameters of the optimization problem. The manner in which the hyperparameters of IRES are defined is intuitive and bares physical meaning and thus tuning the hyperparameters can be done easily and objectively (as opposed to hyperparameters that are merely mathematical).

In practice EEG/MEG signals arise from the mass response of a large number of neurons which fire synchronously. Thus it is reasonable to assume that variations within the source extent, are hard to be detected from EEG/MEG recordings. Even in data recorded from intracranial EEG the region defined as SOZ by the physician seem to have a uniform activity, i.e., piecewise continuous activity over the recording grid. From a simplistic modeling point of view (and as a first step) the assumption is defendable. Face-based wavelets and spherical wavelet transforms have also been used to model sources but none of the clinical data analysis presented in these approaches shows solutions with varying amplitudes.

Because of the geometrical complexities of the cortex, in certain brain applications, IRES provides information regarding the extent of the underlying source, but it is dealing with an underdetermined system and thus the extent information is not exact. Referring to FIGS. 7 to 10 it can be seen that there is still a noticeable amount of variance in extent estimation. But the general trend of IRES in estimating the extent is correct and distinguishes between sources with extents as small as 8 mm to as large as 50 mm.

The accuracy of ESI results can vary depending on the source location and orientation. It is well-known that deep sources are more difficult to resolve than superficial sources. This adds further complexity to the already difficult inverse problem. Some difficult cases where the simulated sources were deep or more tangentially located (in the inter-hemisphere wall or on the medial wall of the temporal lobe) are presented as examples in FIG. 17 (these cases are included in the statistical results presented so far). As seen in the first row image, in highly noisy conditions (SNR of 6 dB, third column), determining the extent or shape of the source is difficult. IRES nonetheless provides useful information on the location and extent of the source in these very difficult conditions. In less noisy conditions (second row), IRES does well.

Although the CVX software, a general solver for convex optimization problems, was used, other solvers and algorithms include the alternating direction method of multipliers (ADMM) and the fast iterative shrinkage thresholding algorithm (FISTA). Implementing these algorithms for solving IRES can improve the speed and efficiency of the solver (compared to general solvers such as CVX), as demonstrated in the FAST-IRE S algorithm discussed previously.

The idea of trying to determine the underlying epileptic source is important since one third of epilepsy patients do not respond to medication. Surgical resection is a viable option for patients with focal epilepsy within this pharmacoresistant population. Currently the gold standard is to use intracranial EEG to determine SOZ. This is highly invasive with all the risks associated with such procedures. Being able to non-invasively determine the SOZ and assist the physician in determining the location and size of the epileptogenic tissue can improve the quality of life for many patients. Multiple patients have been studied for potential clinical application of IRES to localize and image epileptogenic zone in patients, and IRES may be useful in aiding pre-surgical planning in epilepsy patients.

In certain disclosed implementations, the solution space was limited to the cortical space in examples shown, but the approach is applicable to sub-cortical sources as well. Implementations of IRES have been tested extensively for single time-points as well as spatio-temporal sources to show the feasibility of this algorithm and its applicability in real data recordings. A spatio-temporal framework with efficient implementation was also tested in computer simulations and patient data. Spatio-temporal algorithms are important as the dynamics of the underlying brain sources captured by EEG/MEG has to be studied properly to better understand brain networks. A temporal basis can be extracted from the EEG recordings onto which the data is projected. This basis can be derived from principle component analysis (PCA), independent component analysis (ICA) and time-frequency analysis of the data. In any case, IRES can be incorporated into the spatio-temporal basis and by no means is limited to single time-points, as discussed in detail above. Presented above are the IRES strategy and results for single time-points source imaging as well as the spatio-temporal source imaging.

Figure 28:
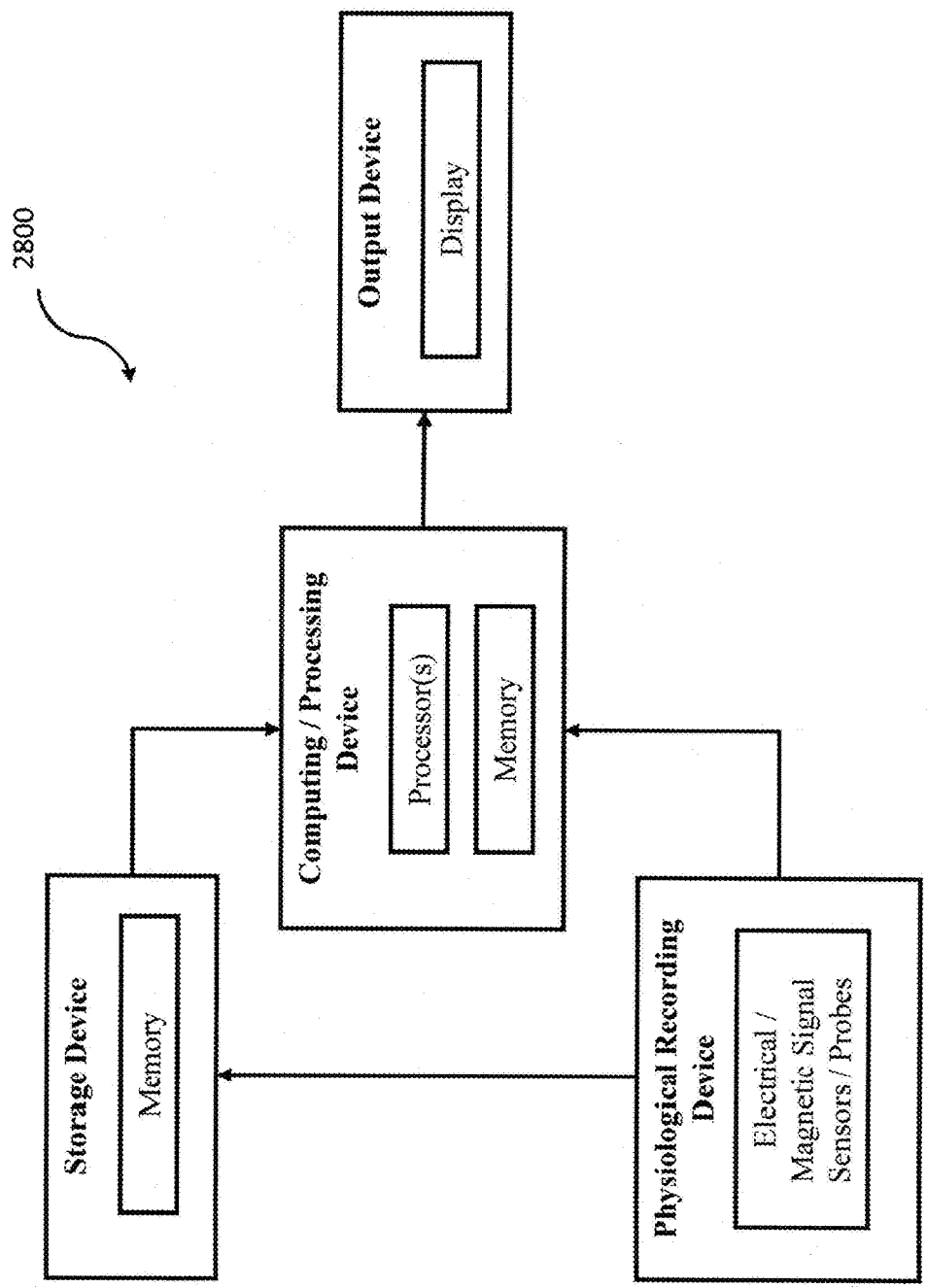
FIG. 28 depicts an example system that could be used to implement the disclosed approaches in one or more embodiments.

Referring to FIG. 28, in example embodiments, the disclosed approach may be implemented using system 2800. A computing device includes one or more processors and a memory capable of storing instructions executable by the processors. These instructions may include, for example, instructions for the computations/algorithms disclosed above (such as imposing edge sparsity and the iterative reweighting), as well as instructions for inputting data (such as recorded electrical signals) and outputting data (such as generated source distribution images). The computing device may receive physiological data from a physiological recording device (which may be, for example, an EEG or MEG device, etc.) that can record electrical or magnetic signals using multiple sensors/probes (such as the electrodes). The computing device may also receive recorded electrical or magnetic signals via a storage device having memory capable of storing electrical signals recorded using the electrical signal sensors of the physiological recording device. The computing device may process the signals and generate an image, a series of images, a movie, etc., and provide images/movies to an output device that may include a display screen for visually depicting a three-dimensional representation of the location and extent of sources determined using the recorded electrical/magnetic signals. It is noted that not all components and devices that can be used to implement the disclosed embodiments are shown. For example, not shown are auxiliary input devices (such as a keyboard, computer mouse, touchscreen display, etc.) that can allow a user to, for example, initiate recording of electrical/magnetic signals, transfer data between devices, initiate processing, tailor the generated images, etc.

APPENDIX A—EXAMPLE WEIGHTING STRATEGY FOR IRES

Assuming that our problem is the following, where C is a convex set:

$$x^{est} = \operatorname*{argmin}_{x} \|x\|_1 \quad \text{(A1)}$$

subject to $x \in C$

It is reformulated as follows where E is a positive number, $$\operatorname{argmin} \ln\left(\frac{|x|}{\epsilon} + 1\right) \; x \in C \quad \text{(A2)}$$

In order to solve (A2) we linearize the logarithm function about the solution obtained in the previous step using the Taylor expansion's series as follows, $$x^{k+1} = \operatorname*{argmin}_{x} \ln\left(\frac{|x|}{\epsilon} + 1\right) \; x \in C \quad \text{(A3)}$$

$$\ln\left(\frac{|x|}{\epsilon} + 1\right) = \ln\left(\frac{|x^k|}{\epsilon} + 1\right) + \frac{1}{\epsilon} \cdot \left(\frac{1}{\frac{|x^k|}{\epsilon} + 1}\right) \cdot (x - x^k) + O((x - x^k)^2)$$

Substituting the linearized logarithm into the optimization problem and noting that $x^k$ is treated as a constant (as the minimization is with respect to x) the following optimization problem is achieved, $$x^{k+1} = \operatorname*{argmin}_{x}\left(\frac{x}{\frac{|x^k|}{\epsilon} + 1}\right) = \operatorname*{argmin}_{x} W^k x \text{ s.t. } x \in C \quad \text{(A4)}$$

$$W^k = \left(\frac{1}{\frac{|x^k|}{\epsilon} + 1}\right)$$

Note that x was treated as a scalar here. In our case where x is a vector the weighting is derived for each element individually and finally placed into a diagonal matrix format. This is how (3) is derived. Treating (Vj) as a vector, i.e. y=Vj, the same procedure can be followed to update $W_d$.

APPENDIX B—EXAMPLE VECTOR-BASED ITERATIVELY REWEIGHTED EDGE SPARSITY MINIMIZATION (VIRES)

Applying the same idea as in IRES to the case where the orientation is not fixed will now be discussed. It may be assumed that each of the three dimensions of the dipole is an independent variable; in that case the procedure described in Appendix A and (3) should be followed. Another way to approach the problem is to penalize the amplitude of the vector in the penalization terms as the variable under study is a vector now. It should be noted that matrix V which approximates the discrete gradient should be expanded three times using the Kronecker product, $V_{New} = V \otimes I_3$ where $I_3$ is the 3×3 identity matrix. Following what was derived in (3), the following can be derived, $$j^L = \operatorname*{argmin}_{j} \sum_{i=1}^{T} W_d^{L-1}(i,i) \|V_{New(i,:)} j\|_2 + \quad \text{(B1)}$$

$$\alpha \sum_{p=1}^{n} W^{L-1}(p,p) \|[j_p(x), j_p(y), j_p(z)]\|_2$$

subject to $(\varphi - Kj)^T \sum^{-1} (\varphi - Kj) \leq \beta$ $W^L, W_d^L \to$ Updated based on $j^L$ Where T is the number of edges and n is the number of dipole locations. Also $V_{New\,(i,:)}$ denotes the rows of $V_{New}$ that correspond to the $i^{th}$ edge. These correspond to the $3*i-2^{th}$ to the $3*i^{th}$ rows of $V_{New}$.

Following the steps in Appendix A, the update rule for the weights at iteration L can be obtained as follows, $$W^L(p,p) = \left(\frac{1}{\frac{\|[j_p^{L-1}(x),\, j_p^{L-1}(y),\, j_p^{L-1}(z)]\|_2}{\epsilon} + 1}\right) \quad \text{(B2)}$$

for $p = 1, 2, \ldots, n$ $$W_d^L(i,i) = \left(\frac{1}{\frac{\|V_{New(i,:)} j^{L-1}\|_2}{\epsilon} + 1}\right) \quad \text{(B3)}$$

for $i = 1, 2, \ldots, T$

Following the multiple domain sparsity in the regularization terms, the optimization problem can be formulated as a second order cone programming (SOCP) in (2). While problems involving L1 norm minimization do not have closed-form solutions and may seem complicated, such problems can readily be solved as they fall within the convex optimization category. There are many efficient methods for solving convex optimization problems.

As suggested, estimating extended brain sources using EEG/MEG source imaging techniques is challenging. EEG and MEG have excellent temporal resolution at millisecond scale but their spatial resolution is limited due to the volume conduction effect. Sparse signal processing techniques have been exploited to impose sparsity on the underlying source and its transformation in other domains (mathematical domains, like spatial gradient). Using an iterative reweighting strategy to penalize locations that are less likely to contain any source, it is shown that the disclosed IRES strategy can provide reasonable information regarding the location and extent of the underlying sources. This approach is unique in part because it estimates extended sources without the need of subjectively thresholding the solution. As discussed, the performance of IRES has been evaluated in a series of computer simulations. Different parameters such as source location and signal-to-noise ratio were varied and the estimated results were compared to the targets using metrics such as localization error (LE), area under curve (AUC) and overlap between the estimated and simulated sources. It is shown that IRES provides extended solutions which not only localize the source but also provide estimation for the source extent. The performance of IRES was further tested in epileptic patients undergoing intracranial EEG (iEEG) recording for pre-surgical evaluation. IRES was applied to scalp EEGs during interictal spikes, and results were compared with iEEG and surgical resection outcome in the patients. Clinical study results demonstrate a good concordance between noninvasive IRES source estimation with iEEG and surgical resection outcomes in the same patients. The disclosed approach, i.e. IRES, can estimate extended source solutions from scalp electromagnetic signals which provide relatively accurate information about the location and extent of the underlying source.

Electrophysiological source imaging has also been pursued to image cardiac electrical activity from electrocardiography (ECG) or magnetocardiography (MCG) measurements. Cardiac excitation and repolarization corresponding to normal and abnormal cardiac functions generate electrical activity that can be measured using noninvasive electrical or magnetic sensors. Equivalent source distributions including electrical potentials, current dipoles, or monopoles have been used to represent cardiac electrical activity, and estimated from ECG or MCG. Such cardiac equivalent sources can be distributed over the epicardial surface, the epicardial and endocardial surfaces, or the three-dimensional myocardial volume. Similar to brain source imaging problem, one needs to determine objectively the volume or area of cardiac electrical activity from estimated solutions using ECG/MCG.

Electrophysiological source imaging may also be applied to imaging of muscular electrical activity from electrical or magnetic recordings, or from other organs of a biological system.

The present invention has been described in terms of one or more preferred embodiments, and it should be appreciated that many equivalents, alternatives, variations, additions, and modifications, aside from those expressly stated, and apart from combining the different features of the foregoing embodiments in varying ways, can be made and are within the scope of the invention. In the above description, a number of specific details, examples, and scenarios are set forth in order to provide a better understanding of the present disclosure. These examples and scenarios are provided for illustration, and are not intended to limit the disclosure in any way. The true scope of the invention will be defined by the claims included in this and any later-filed patent applications in the same family.

Those of ordinary skill in the art, with the included descriptions, will be able to implement appropriate functionality without undue experimentation. References in the specification to an "embodiment," an "example," a "version," an "implementation," a "configuration," an "instance," an "iteration," etc., indicate that the embodiment, example, version, etc. described may include one or more particular features, structures, or characteristics, but not every embodiment, example, version, etc. necessarily incorporates the particular features, structures, or characteristics. Further, when a particular feature, structure, or characteristic is described in connection with an embodiment, it is believed to be within the knowledge of one skilled in the art to effect such feature, structure, or characteristic in connection with other embodiments whether or not explicitly indicated.

The computerized functionality described above may be implemented in hardware, firmware, software, single integrated devices, multiple devices in wired or wireless communication, or any combination thereof. Computerized functions may be implemented as instructions stored using one or more machine-readable media, which may be read and executed by one or more processors. A machine-readable medium may include any mechanism for storing or transmitting information in a form readable by a machine. For example, a machine-readable medium may include any suitable form of volatile or non-volatile memory. In the drawings, specific arrangements or orderings of schematic elements may be shown for ease of description. However, the specific ordering or arrangement of such elements is not meant to imply that a particular order or sequence of processing, or separation of processes, is required in all embodiments. Further, some connections or relationships between elements may be simplified or not shown in the drawings so as not to obscure the disclosure. This disclosure is to be considered as exemplary and not restrictive in character, and all changes and modifications that come within the spirit of the disclosure are desired to be protected.

The invention claimed is:

1. A system for three-dimensional electrical source imaging of electrical activity in a biological system, the system comprising:
a sensor array configured to record, at multiple locations, signals of electrical activity in the biological system;
a processor configured to:
control the sensor array to record the signals of electrical activity in the biological system;
generate an initial estimate of a spatial extent of an underlying source based on the signals of electrical activity;
impose edge sparsity on the initial estimate to eliminate background activity and create clear edges between an active source and background activity;
iteratively reweight the edge sparsity of the initial estimate and launch a series of subsequent optimization problems to converge to a more accurate estimation of the spatial extent of the underlying source, wherein the locations having smaller source amplitude are penalized based on solutions obtained in previous iterations;

generate one or more images depicting the spatial extent of the underlying source in the biological system using the iteratively reweighted edge sparsity; and generate one or more time courses of electrical activity depicting temporal dynamics of the underlying source in the biological system using the iteratively reweighted edge sparsity.

2. The system of claim 1, wherein the processor is configured to generate the one or more images without application of a subjective threshold requirement for a magnitude of an electrical activity characteristic.

3. The system of claim 1, wherein the iterative reweighting continues until a solution is obtained with clear edges from the background activity.

4. The system of claim 1, wherein the processor is configured to generate a series of images or a movie depicting spread, in time, of electrical activity, and time-course of electrical activity through the biological system.

5. The system of claim 1, wherein the processor, when imposing the edge sparsity, imposes sparsity on both a solution and a spatial gradient of the solution to estimate the spatial extent of the underlying source.

6. The system of claim 1, wherein the biological system is a brain, and wherein the sensor array is configured to record electrical signals of electrical activity in the brain of a subject.

7. The system of claim 1, wherein the biological system is a brain, and wherein the sensor array is configured to record magnetic signals of electrical activity in the brain of a subject.

8. The system of claim 1, wherein the biological system is a brain, and wherein the sensor array is configured to record both electrical and magnetic signals of electrical activity in the brain of a subject.

9. The system of claim 1, wherein the biological system is a brain with epileptic disorder, and wherein the generated source images are used to determine an epileptogenic region of the brain of a subject guiding interventions.

10. The system of claim 1, wherein the biological system is a heart, and wherein the sensor array is configured to record electrical signals of electrical activity in the heart of a subject.

11. The system of claim 1, wherein the biological system is a heart with arrhythmia, and wherein the generated source images are used to determine origins of arrhythmia and arrhythmogenetic regions of the heart of a subject.

12. The system of claim 1, wherein the generated one or more images visually depict location and extent of an electrical source at a given time.

13. The system of claim 1, wherein the processor is configured to obtain the spatial extent of the underlying source by adding an edge-sparse term into a source optimization solution.

14. The system of claim 1, wherein the processor is further configured to display the generated one or more images and their related time-course of electrical activity on a display device.

15. A method for three-dimensional source imaging of electrical activity in a biological system, the method comprising:

receiving signals of electrical activity recorded, using a sensor array, at multiple locations in the biological system;

generating an initial estimate of a spatial extent of an underlying source based on the signals of electrical activity;

imposing edge sparsity on the initial estimate to eliminate background activity and create clear edges between an active source and background activity;

iteratively reweighting the edge sparsity of the initial estimate and launching a series of subsequent optimization problems to converge to a more accurate estimation of a spatial extent of the underlying source, wherein the locations having smaller source amplitude are penalized based on solutions obtained in previous iterations;

generating one or more images depicting the spatial extent of the underlying source in the biological system using the iteratively reweighted edge sparsity; and estimating one or more time courses of electrical activity depicting temporal dynamics of the underlying source in the biological system using the iteratively reweighted edge sparsity.

16. The method of claim 15, wherein the one or more images are generated without application of a subjective threshold requirement for a magnitude of an electrical activity characteristic.

17. The method of claim 15, wherein the iterative reweighting continues until a solution is obtained with clear edges from the background activity.

18. The method of claim 15, wherein the one or more images depict spread, in time, of electrical activity, and time-course of electrical activity through the biological system.

19. The method of claim 15, wherein imposing the edge sparsity further comprises imposing sparsity on both a solution and a spatial gradient of the solution to estimate the spatial extent of the underlying source.

20. The method of claim 15, wherein the biological system is a brain, and wherein the sensor array records electrical signals of electrical activity in the brain of a subject.

21. The method of claim 15, wherein the biological system is a brain, and wherein the sensor array records magnetic signals of electrical activity in the brain of a subject.

22. The method of claim 15, wherein the biological system is a brain, and wherein the sensor array records both electrical and magnetic signals of electrical activity in the brain of a subject.

23. The method of claim 15, wherein the biological system is a brain with epileptic disorder, and wherein the generated source images are used to determine an epileptogenic region of the brain of a subject guiding interventions.

24. The method of claim 15, wherein the biological system is a heart, and wherein the sensor array records electrical signals of electrical activity in the heart of a subject.

25. The method of claim 15, wherein the biological system is a heart with arrhythmia, and wherein the generated source images are used to determine origins of arrhythmia and arrhythmogenetic regions of the heart of a subject.

26. The method of claim 15, wherein the generated one or more images visually depict location and extent of an electrical source at a given time and its related time-course of electrical activity.

27. The method of claim 15, wherein the processor is configured to obtain the spatial extent of the underlying source by adding an edge-sparse term into a source optimization solution.

28. A non-volatile storage medium having instructions for three-dimensional source imaging of electrical activity in a biological system, wherein the instructions, when executed by a processor, are configured to:
- receive signals of electrical activity recorded, using a sensor array, at multiple locations in the biological system;
- generate an initial estimate of an underlying source;
- impose edge sparsity on the initial estimate to eliminate background activity and create clear edges between an active source and background activity;
- iteratively reweight the edge sparsity of the initial estimate and launch a series of subsequent optimization problems to converge to a more accurate estimation of a spatial extent of the underlying source,
  - wherein the locations having smaller source amplitude are penalized based on solutions obtained in previous iterations;
- generate one or more images depicting the spatial extent of the underlying source in the biological system using the iteratively reweighted edge sparsity; and
- generate one or more time courses of electrical activity depicting temporal dynamics of the underlying source in the biological system using the iteratively reweighted edge sparsity.

* * * * *

UNITED STATES PATENT AND TRADEMARK OFFICE
CERTIFICATE OF CORRECTION

PATENT NO. : 10,945,622 B2
APPLICATION NO. : 15/684394
DATED : March 16, 2021
INVENTOR(S) : Abbas Sohrabpour et al.

Page 1 of 1

It is certified that error appears in the above-identified patent and that said Letters Patent is hereby corrected as shown below:

In the Specification

Column 2, Line 55, "the norm" should be --the L1 norm--.

Column 15, Line 17, Eq. (6), " $j^L = \arg\min_j \sum_{i=1}^{N_c} \|W_{d,i}^{L-1}(Vj_{\cdot}) + \sum_{i=1}^{N_c} \alpha_i \| W_i^{L-1} j_{\cdot} \|_1$ " should be
-- $j^L = \arg\min_j \sum_{i=1}^{N_c} \|W_{d,i}^{L-1}(Vj_{\cdot}) + \sum_{i=1}^{N_c} \alpha_i \| W_i^{L-1} j_{\cdot} \|_1$ --.

Column 16, Line 21, "a$_i$(t)" should be --α$_i$(t)--.

Column 16, Line 48, Eq. (9), " $j^L = \arg\min_j \sum_{i=1}^{N_c} \|W_{d,i}^{L-1}(Vj_{\cdot})\|_1 + \sum_{i=1}^{N_c} \alpha_i \| W_i^{L-1} j_{\cdot} \|_1$ " should be
-- $j^L = \arg\min_j \sum_{i=1}^{N_c} \|W_{d,i}^{L-1}(Vj_{\cdot})\|_1 + \sum_{i=1}^{N_c} \alpha_i \| W_i^{L-1} j_{\cdot} \|_1$ --.

Column 30, Line 35, "FAST-IRE S" should be --FAST-IRES--.

Column 31, Line 49, "where E is" should be --where ε is--.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*